(12) United States Patent
Southard et al.

(10) Patent No.: US 7,976,847 B2
(45) Date of Patent: Jul. 12, 2011

(54) CONTROLLED RELEASE CGRP DELIVERY COMPOSITION FOR CARDIOVASCULAR AND RENAL INDICATIONS

(75) Inventors: Jeffrey L. Southard, Lenexa, KS (US); George L. Southard, Sanibel, FL (US)

(73) Assignee: VasoGenix Pharmaceuticals, Inc., Lenexa, KS (US)

( * ) Notice: Subject to any disclaimer, the term of this patent is extended or adjusted under 35 U.S.C. 154(b) by 808 days.

(21) Appl. No.: 10/586,209

(22) PCT Filed: Jan. 13, 2005

(86) PCT No.: PCT/US2005/001225
§ 371 (c)(1),
(2), (4) Date: Nov. 8, 2007

(87) PCT Pub. No.: WO2005/067890
PCT Pub. Date: Jul. 28, 2005

(65) Prior Publication Data
US 2008/0069865 A1    Mar. 20, 2008

Related U.S. Application Data

(60) Provisional application No. 60/560,745, filed on Jan. 13, 2004.

(51) Int. Cl.
*A61K 38/23* (2006.01)
*A61K 9/52* (2006.01)

(52) U.S. Cl. .................... 424/198.1; 424/489

(58) Field of Classification Search .................... None
See application file for complete search history.

(56) References Cited

U.S. PATENT DOCUMENTS

| | | | |
|---|---|---|---|
| 3,523,906 A | 8/1970 | Vrancken et al. |
| 3,737,337 A | 6/1973 | Schnoring et al. |
| 3,773,919 A | 11/1973 | Boswell et al. |
| 4,179,337 A | 12/1979 | Davis et al. |
| 4,272,398 A | 6/1981 | Jaffe |
| 4,627,839 A | 12/1986 | Young |
| 4,720,483 A | 1/1988 | Jansz et al. |
| 4,764,378 A | 8/1988 | Keith et al. |
| 4,797,285 A | 1/1989 | Barenholz et al. |
| 4,938,763 A | 7/1990 | Dunn et al. |
| 4,957,119 A | 9/1990 | de Nijs |
| 5,019,400 A | 5/1991 | Gombotz et al. |
| 5,023,252 A | 6/1991 | Hseih |
| 5,088,505 A | 2/1992 | De Nijs |
| 5,126,134 A | 6/1992 | Heim et al. |
| 5,190,761 A | 3/1993 | Liburdy |
| 5,271,961 A | 12/1993 | Mathiowitz et al. |
| 5,324,519 A | 6/1994 | Dunn et al. |
| 5,336,489 A | 8/1994 | Strom |
| 5,637,309 A | 6/1997 | Tajima et al. |
| 5,702,716 A | 12/1997 | Dunn et al. |
| 5,728,396 A | 3/1998 | Peery et al. |
| 5,744,153 A | 4/1998 | Yewey et al. |
| 5,820,589 A | 10/1998 | Torgerson et al. |
| 5,863,554 A | 1/1999 | Illum |
| 5,910,482 A | 6/1999 | Yallampalli et al. |
| 5,958,877 A | 9/1999 | Wimalawansa |
| 5,985,305 A | 11/1999 | Peery et al. |
| 5,990,194 A | 11/1999 | Dunn et al. |
| 6,143,314 A | 11/2000 | Chandrashekar et al. |
| 6,201,072 B1 | 3/2001 | Rathi et al. |
| 6,306,406 B1 | 10/2001 | Deluca |
| 6,358,247 B1 | 3/2002 | Altman et al. |
| 6,403,114 B1 | 6/2002 | Rickey et al. |
| RE37,950 E | 12/2002 | Dunn et al. |
| 6,503,534 B1 | 1/2003 | Pellet et al. |
| 6,525,102 B1 | 2/2003 | Chen et al. |
| 6,528,080 B2 | 3/2003 | Dunn et al. |
| 6,544,252 B1 | 4/2003 | Theeuwes et al. |
| 6,555,156 B1 | 4/2003 | Loughman |
| 6,565,874 B1 | 5/2003 | Dunn et al. |
| 6,582,080 B2 | 6/2003 | Gibbon et al. |
| 6,589,549 B2 | 7/2003 | Shih et al. |
| 6,809,079 B2 | 10/2004 | Southard et al. |
| 2008/0097503 A1 | 4/2008 | Creaven |
| 2009/0023643 A1 | 1/2009 | Southard et al. |
| 2009/0023644 A1 | 1/2009 | Southard et al. |

FOREIGN PATENT DOCUMENTS

| | | |
|---|---|---|
| EP | 0 467 389 A2 | 1/1992 |
| EP | 0 467 389 A3 | 1/1992 |
| EP | 0 539 751 A1 | 5/1993 |
| EP | 0 539 751 B1 | 5/1993 |
| EP | 0 645 136 A2 | 3/1995 |
| EP | 0 645 136 A3 | 3/1995 |
| EP | 0 765 659 A1 | 4/1997 |
| EP | 0 845 269 A2 | 6/1998 |
| EP | 0 845 269 A3 | 6/1998 |
| JP | 4-503163 A | 6/1992 |

(Continued)

OTHER PUBLICATIONS

Asahina, A. et al. (Aug. 1995). "Specific Induction of cAMP in Langerhans Cells by Calcitonin Gene-Related Peptide: Relevance to Functional Effects," *PNAS USA* 92:8323-8327.

(Continued)

*Primary Examiner* — Ruixiang Li
(74) *Attorney, Agent, or Firm* — Schwegman, Lundberg & Woessner, P.A.

(57) ABSTRACT

The present invention provides methods of treating heart failure and improving renal function, and/or preventing the advancement of heart failure into advanced stages, and methods of counteracting ischemia due to a myocardial infarction by providing improved methods of administering a therapeutically effective amount CGRP as a controlled release formulation. The therapies can be administered on an outpatient or inpatient basis and can further be used as maintenance therapies.

26 Claims, No Drawings

FOREIGN PATENT DOCUMENTS

| | | | |
|---|---|---|---|
| JP | 5-103838 A | 4/1993 |
| JP | 5-305135 A | 11/1993 |
| JP | 7-89876 A | 4/1995 |
| JP | 9-511741 A | 11/1997 |
| JP | 2002-501908 A | 1/2002 |
| JP | 2002-516910 A | 6/2002 |
| JP | 2002-528403 A | 9/2002 |
| JP | 2003-104913 A | 4/2003 |
| WO | WO-90/03768 A1 | 4/1990 |
| WO | WO-93/23011 A1 | 11/1993 |
| WO | WO-95/27481 A1 | 10/1995 |
| WO | WO-96/30013 A1 | 10/1996 |
| WO | WO-99/18142 A1 | 4/1999 |
| WO | WO-99/38536 A1 | 8/1999 |
| WO | WO-00/24374 A1 | 5/2000 |
| WO | WO-02/098446 A1 | 12/2002 |
| WO | WO-03/059250 A2 | 7/2003 |
| WO | WO-03/059250 A3 | 7/2003 |
| WO | WO-03/063799 A2 | 8/2003 |
| WO | WO-03/063799 A3 | 8/2003 |
| WO | WO-03/013538 A1 | 12/2003 |
| WO | WO-2005/067890 A2 | 7/2005 |
| WO | WO-2005/067890 A3 | 7/2005 |
| WO | WO-2005/070444 A2 | 8/2005 |
| WO | WO-2005/070444 A3 | 8/2005 |
| WO | WO-2005/070444 C1 | 8/2005 |
| WO | WO-2005/070445 A2 | 8/2005 |
| WO | WO-2005/070445 A3 | 8/2005 |
| WO | WO-2006/029320 A1 | 3/2006 |

OTHER PUBLICATIONS

Brindis, R.G. et al. (Jun. 15, 2001). "The American College of Cardiology-National Cardiovascular Data Registry™ (ACC-NCDR™): Building a National Clinical Data Repository," *Journal of the American College of Cardiology* 37(8):2240-2245.

Chai, W. et al. (Feb. 15, 2006, e-pub. Jan. 24, 2006). "The Role of Calcitonin Gene-Related Peptide (CGRP) in Ischemic Preconditioning in Isolated Red Hearts," European Journal of Pharmacology 531 (1-3):246-253.

Duzendorfer, S. et al. (2002-2003). "Neuropeptide-Induced Inhibition of IL-16 Release from Eosinophils," *NeuroImmunoModulation* 10:217-223.

Feng, Y. et al. (1997). "Inhibition of LPS-Induced TNF-α Production by Calcitonin Gene-Related Peptide (CGR) in Cultured Mouse Peritoneal Macrophages," *Life Sciences* 61(20):PL-281-PL-287.

Fernandez, S. et al. (May 2000). "Calcitonin-Gene Related Peptide (CGRP) Inhibits Interleukin-7-Induced Pre-B Cell Colony Formation," *Journal of Leukocyte Biology* 67:669-676.

Foncea, R. et al. (Aug. 1, 1997). "Insulin-Like Growth Factor-I Rapidly Activates Multiple Signal Transduction Pathways in Cultured Rat Cardiac Myocytes," *J. Biol. Chem.* 272(31):19115-19124.

GenBank Accession No. 1005250A, last updated May 8, 1996, located at <http://www.ncbi.nlm.nih.gov/protein/223948?report=genpept>, last visited on Apr. 28, 2009, 2 pages.

International Search Report mailed on Jul. 5, 2006, for PCT Application No. PCT/US2005/001230, filed on Jan. 13, 2005, two pages.

International Search Report mailed on Oct. 5, 2006, for PCT Application No. PCT/US2005/001224, filed on Jan. 13, 2005, five pages.

Morris, H.R. et al. (Apr. 1984). "Isolation and Characterization of Human Calcitonin Gene-Related Peptide," *Nature* 308:746-748.

Nishikimi, T. et al. (Jul. 24, 1998). "Effect of Adrenomedullin on cAMP and cGMP Levels in Rat Cardiac Myocytes and Nonmyocytes," *Eur. J. Pharmacol.* 353(2/3):337-344.

Scanlon, P.J. et al. (1999). "ACC/AGA Guidelines for Coronary Angiography: A Report of The American College of Cardiology/American Heart Association Task Force on Practice Guidelines, (Committee on Coronary Angiography)" *The Journal of the American College of Cardiology* 33(6):1756-17824.

Torii, H. et al. (Feb. 1997). "Regulation of Cytokine Expression in Macrophages and the Langerhans Cell-Like Line XS52 by Calcitonin Gene-Related Peptide," *Leukoc. Biol.* 61:216-223.

Wolfrum, S. et al. (Apr. 15, 2005). "Calcitonin Gene Related Peptide Mediates Cardioprotection by Remote Preconditioning," *Regulatory Peptides* 127 (1-3):217-224.

Written Opinion mailed on Jul. 5, 2006, for PCT Application No. PCT/US2005/001230, filed on Jan. 13, 2005, nine pages.

Written Opinion mailed on Oct. 5, 2006, for PCT Application No. PCT/US2005/001224, filed on Jan. 13, 2005, seven pages.

Anand, I.S. at al. (Jan. 1991). "Cardiovascular and Hormonal Effects of Calcitonin Gene-Related Peptide in Congestive Heart Failure," *J. Am. Coll. Cardiol.* 17(1):208-217.

Anonymous (May 1990). *The FASEB Journal* 4(8):2544.

Benita, S. et al. (Dec. 1984). "Characterization of Drug-Loaded poly($d,l$-lactide) Microspheres," *Journal of Pharmaceutical Sciences* 73(12):1721-1724.

Fleisher, D. et al. (May 22, 1996). "Improved Oral Drug Delivery: Solubility Limitations Overcome by the Use of Prodrugs," *Advanced Drug Delivery Reviews* 19(2):115-130.

Gennari, C. et al. (Mar. 1990). "Improved Cardiac Performance with Human Calcitonin Gene Related Peptide in Patients with Congestive Heart Failure," *Cardiovascular Res.* 24(3):239-241.

Haegerstrand, A. et al. (May 1990). "Calcitonin Gene-Related Peptide Stimulates Proliferation of Human Endothelial Cells," *Proc. Natl. Acad. Sci. USA* 87(9):3299-3303.

Hunt, S.A. et al. (2001). *ACC/AHA Practice Guidelines: ACC/AHA Guidelines for the Evaluation and Management Chronic Heart Failure in the Adult*, American College of Cardiology and the American Heart Association, Inc., ed., pp. 1-56.

International Search Report mailed on Jul. 20, 2006, for PCT Application No. PCT/US2005/001225, filed on Jan. 13, 2005, five pages.

Kakeya, N. et al. (Feb. 1984). "Studies on Prodrugs of Cephalosporins. I. Synthesis and Bbiological Properties of Glycyloxybenzoyloxymethyl and Glycylaminobenzoyloxymethyl Esters of 7 β-[2-(2- aminothiazol-4-yl)-(Z)-2-methoxyiminoacetamido]-3- methyl-3-cephem-4-carboxylic acid," *Chem. Pharm. Bull.* 32(2):692-698.

Lu, E-X. et al. (Dec. 1996). "Calcitonin Gene-Related Peptide-Induced Preconditioning Improves Preservation with Cardioplegia," *Ann. Thorac. Surg.* 62:1748-1751.

March, K.L. et al. (Jan. 1995). "Pharmacokinetics of Adenoviral Vector-Mediated Gene Delivery to Vascular Smooth Muscle Cells: Modulation by Poloxamer 407 and Implications for Cardiovascular Gene Therapy," *Human Gene Therapy* 6(1):41-53.

Mathiowitz, E. et al. (1987). "Novel Microcapsules for Delivery Systems," *Reactive Polymers* 6:275-283.

Mathiowitz, E. et al. (1987). "Polyanhydride Microspheres as Drug Carriers. I. Hot-Melt Microencapsulation," *Journal of Controlled Release* 5:13-22.

Mathiowitz, E. et al. (Feb. 20, 1988). "Polyanhydride Microspheres as Drug Carriers. II. Microencapsulation by Solvent Removal," *Journal of Applied Polymer Science* 35(3):755-774.

Mathiowitz, E. et al. (1990). "Morphology of Polyanhydride Microsphere Delivery Systems," *Scanning Microscopy* 4(2):329-340.

Mathiowitz, E. et al. (May 5, 1992). "Polyanhydride Microspheres. IV. Morphology and Characterization of Systems Made by Spray Drying," *Journal of Applied Polymer Science* 45(1):125-134.

Merrifield, R.B. (Jul. 20, 1963). "Solid Phase Peptide Synthesis. I. The Synthesis of a Tetrapeptide," *Journal of the American Chemical Society* 85(14):2149-2154.

Merrifield, R.B. (Apr. 18, 1986). "Solid Phase Synthesis," *Science* 232(4748):341-347.

Nielsen, N.M. et al. (Apr. 1988). "Glycolamide Esters as Biolabile Prodrugs of Carboxylic Acid Agents: Synthesis, Stability, Bioconversion, and Physicochemical Properties," *Journal of Pharmaceutical Sciences* 77(4):285-298.

Robinson, R.P. (Jan. 5, 1996). "Discovery of the Hemifumarate and (alpha-L-alanyloxy)methyl ether as Prodrugs of an Antirheumatic Oxindole: Prodrugs for the Enolic OH Group," *J. Med. Chem* 39(1):10-18.

Shekhar, Y.C. et al. (Apr. 1, 1991). "Effects of Prolonged Infusion of Human Alpha Calcitonin Gene-Related Peptide on Hemodynamics, Renal Blood Flow and Hormone Levels in Congestive Heart Failure," *Am. J. Cardiol.* 67:732-735.

Shimizu, K. et al. (Dec. 3/17, 1999). "Adrenomedullin Receptor Antagonism by Calcitonin Gene-Related Peptide (8-37) Inhibits Carotid Artery Neointimal Hyperplasia after Balloon Injury," *Circulation Research* 85:1199-1205.

Stevenson, R.N. et al. (Dec. 1992). "Calcitonin Gene-Related Peptide: A Haemodynamic Study of a Novel Vasodilator in Patients with Severe Chronic Heart Failure," *Intl. J. Cardiol.* 37:407-414.

Wang, C-Y. et al. (Nov. 1987). "pH-sensitive Immunoliposomes Mediate Target-Cell-Specific Delivery and Controlled Expression of a Foreign Gene in Mouse," *Proc. Nat. Acad. Sci. USA* 84:7851-7855.

Wang, C-Y. et al. (Nov. 28, 1989). "Highly Efficient DNA Delivery Mediated by pH-sensitive Immunoliposomes," *Biochemistry* 28(24):9508-9514.

Wimalawansa, S.J. (Oct. 1996). "Calcitonin Gene-Related Peptide and Its Receptors: Molecular Genetics, Physiology, Pathophysiology, and Therapeutic Potentials," *Endocrine Reviews* 17(5):533-585.

Wimalawansa, S.J. (1997). "Amylin, Calcitonin Gene-Related Peptide, Calcitonin, and Adrenomedullin: A Peptide Superfamily," *Critical Reviews in Neurobiology* 11(2-3):167-239.

Written Opinion mailed on Jul. 20, 2006, for PCT Application No. PCT/US2005/001225, filed on Jan. 13, 2005, nine pages.

Zhou, Z-H. et al. (Dec. 2001). "Improvement of Preservation with Cardioplegic Solution by Nitroglycerin-Induced Delayed Preconditioning is Mediated by Calcitonin Gene-Related Peptide," *Int. J. Cardiol.* 81:211-218.

CONTROLLED RELEASE CGRP DELIVERY COMPOSITION FOR CARDIOVASCULAR AND RENAL INDICATIONS

This application is a 371 of PCT/US2005/001225, filed Jan. 13, 2005, which claims the benefit of U.S. Provisional Application Ser. No. 60/560,745, filed Jan. 13, 2004, the disclosure of which is incorporated herein by reference in its entirety.

BACKGROUND OF THE INVENTION

1. Field of the Invention

The present invention provides methods for treating heart failure improving renal function preventing or delaying the advancement of heart failure into advanced stages, and counteracting ischemia due to a myocardial infarction by providing improved methods of administering a therapeutically effective amount CGRP as a controlled release formulation.

2. Description of the Prior Art

Heart failure is a complex clinical syndrome that can result from any structural or functional cardiac disorder that impairs the ability of the ventricle to fill with or eject blood, and the heart works less efficiently than it should. Heart failure is characterized by specific symptoms (e.g., dyspnea and fatigue) which may limit exercise tolerance and signs (e.g., fluid retention) which may lead to pulmonary congestion and peripheral edema. Both abnormalities can impair the functional capacity and quality of life of affected individuals, but they may not necessarily dominate the clinical picture at the same time. Because not all patients have volume overload at the time of initial or subsequent evaluation, the term "heart failure" is preferred over the older term "congestive heart failure."

The clinical syndrome of heart failure may result from disorders of the pericardium, myocardium, endocardium, or great vessel. For example, common causes of heart failure include: narrowing of the arteries supplying blood to the heart muscle (coronary heart disease); prior heart attack (myocardial infarction) resulting in scar tissue large enough to interfere with normal function of the heart; high blood pressure; heart valve disease due to past rheumatic fever or an abnormality present at birth; primary disease of the heart muscle itself (cardiomyopathy); defects in the heart present at birth (congenital heart disease) and infection of the heart valves and/or muscle itself (endocarditis and/or myocarditis or pericarditis). The majority of patients with heart failure have symptoms due to an impairment of left ventricular function. Each of these disease processes can lead to heart failure by reducing the strength and efficiency of the heart muscle contraction, by limiting the ability of the heart's pumping chambers to fill with blood due to mechanical problems or impaired diastolic relaxation, or by filling the chambers with too much blood.

Renal blood flow is also an important factor in the development of the clinical syndrome of heart failure. It is a determinant of some important neurohormonal responses and of salt and water retention. Renal blood flow is reduced in patients with HF, and many patients with HF will also eventually develop renal failure.

There are four stages of heart failure recognized by the American College of Cardiology Guidelines for the Evaluation and Management of Chronic Heart Failure in the Adult. Stage A refers to patients who are at high risk for developing heart failure but have no identified structural or functional abnormalities of the heart and have never shown signs or symptoms of heart failure. If needed, Stage A patients are prescribed ACE inhibitors to lower blood pressure and reduce the heart's work load. Stage B refers to patients who have developed structural heart disease strongly associated with the development of heart failure but have never shown signs or symptoms of heart failure. Stage B patients are typically prescribed ACE inhibitors and beta-blockers that decrease myocardial oxygen demand and thereby ischemia, and reduce heart rate and cardiac work. Stage C refers to current or prior symptoms of heart failure associated with underlying structural disease. Management of HF at Stage C can involve a triple or quadruple drug therapy that includes ACE inhibitors, beta-blockers, diuretics, and Digitalis. Stage D refers to patients with advanced structural heart disease and marked symptoms of heart failure at rest despite maximal medical therapy, requiring specialized intervention. Since HF is a terminal condition, mid and end-stage BF (Stages C and D, respectively) treatment focuses on alleviating symptoms and increasing the patient's quality of life such that they can continue to live a relatively active lifestyle. Successful management of the progression of heart failure and effective treatments to relieve heart failure symptoms are determined by monitoring increases in the heart's ejection fraction, decreases in dyspnea, and changes in the frequency and/or severity of heart failure symptoms. However, while current end-stage drug therapies such as Dobutamine or Milrinone increase the patient's quality of life, they also have been shown to increase mortality.

It is estimated that about four million people in the United States suffer from various degrees of heart failure. Although heart failure is a chronic condition, the disease often requires acute hospital care. Patients are commonly admitted for acute pulmonary congestion accompanied by serious or severe shortness of breath. Acute care for HF accounts for the use of more hospital days than any other cardiac diagnosis, and consumes in excess of seven and one-half billion dollars in the United States annually.

Current research into the treatment of chronic heart failure is focused on providing cardioprotection, myocardial tissue salvage by minimizing or reducing infarction size, and preventing reperfusion injury. Many current drug therapies for treating heart failure address specific clinical aspects associated with myocardial infarction, such as anti-platelet/fibrinolytic, anti-inflammatory, and antioxidant activities. Such drugs include ACE inhibitors to prevent blood vessel constriction and to increase blood flow to the body, diuretics to remove excess fluid, beta blockers to reduce heart work load, calcium channel blockers to increase the blood flow through the heart and prevent vessel constriction, blood thinners to prevent blood clots, and cardiotonics to strengthen the heart's ability to pump blood. Only a few companies to date are developing new drugs that address tissue salvage, however the effectiveness of these drugs remains to be established in the clinic. As with all drugs, these agents must be taken in doses sufficient to ensure their effectiveness. Problematically, however, over-treatment can lead to hypotension, renal impairment, hyponatremia, hypokalemia, worsening heart failure, impaired mental functioning, and other adverse conditions. Surgical treatments include angioplasty, coronary arty by-pass grafts, valve replacement, pacemakers, internal defibrillators, left ventricular assist devices, and heart transplants.

Heart failure is the number one diagnosis for hospital admissions in patients over the age of 65. More than $38.1 billion has been spent annually since 1991 on inpatient and outpatient costs and greater than $500 million on drugs to treat HF. The disorder is the underlying reason for 12 to 15 million office visits each year and 1.7 to 2.6, million hospital admissions each year. Because of the hospitalization costs required to treat a heart failure patient, the current trend is to get HF patients into outpatient care as soon as possible, often within the 48 hours of hospital admission. Specialized outpatient clinics are now available for heart failure patients. The patients typically attend the clinic between one and four times per week to receive intravenous infusions of a prescribed heart failure therapy until hemodynamic symptoms improve.

Calcitonin gene-related peptide ("CGRP") is a 37-amino acid neuropeptide which is the most potent naturally occurring vasodilator peptide in the human body. CGRP is distributed throughout the central and peripheral nervous systems, and is found in areas that ate known to be involved in cardiovascular function (Wimalawansa, S., Critical Reviews in *Neurobiology*, 11:167-239 (1997)). Peripherally, CGRP is found in the heart, particularly in association with the sinoatrial and atrioventricular nodes. In addition, CGRP is found in nerve fibers that form a dense periadventitial network throughout the peripheral vascular system, including the cerebral, coronary, and renal arteries. CGRP has prominent cardiovascular effects, including vasodilation and positive chronotropic and inotropic effects, which may play an important role in normal cardiovascular function (Wimalawansa, S., *Endocrine Reviews*. 17:208:217 (1996)).

When administered, CGRP has pronounced cardiovascular benefits, including vasodilation, ischemic cardioprotection, reduction in infarction size due to heart attack, inhibition of platelet aggregation and smooth muscle cell proliferation which can potentially reduce the incidence of restenosis, increased renal function, and overall increased efficiency of cardiovascular functions. As a result of providing cardioprotection, minimizing reperfusion injury, and reducing infarction size, CGRP also promotes myocardial tissue salvage. CGRP also plays a role in regulating inotropy, chronotropy, microvascular permeability, vascular tone, and angiogenesis. CGRP also has significant advantages over conventional drug treatments. First, CGRP does not produce the potentially dangerous side effects, toxicity and tolerance associated with conventional cardiovascular drugs such as Nitroglycerin, Dobutamine and Natrecor. In fact, CGRP has been reported to down-regulate immune response via inhibition of cytokine release and has been safely administered to immuno-suppressed subjects without the induction of sensitivity. Second, because CGRP has multiple hemodynamic benefits, it can potentially reduce or eliminate the need for drug cocktails to maintain specific hemodynamic functions. Third, the biochemical activity of CORP is mediated through specific receptor binding sites concentrated in the heart, kidneys, and genitalia, and is known, to act on two specific CGRP receptor subtypes located on the surface of the endothelial and smooth muscle cells, respectively. Accordingly, CGRP exhibits virtually no side effects or tolerance when administered systemically.

Studies have demonstrated that acute administration of CGRP can result in increased cardiac performance and reduced systemic resistance in a number of clinical scenarios. For example, Anand, et al. (*J. Am. Coll. Cardiol.*, 17:208-217 (1991)) reported that short-term IV infusions (10 or 20 minutes) of CGRP at rates of 0.8, 3.2, or 16 ng/kg/min (i.e., 56, 224, or 1120 ng/min based on a 70 kg subject) produced beneficial hemodynamic effects such as decreased systemic vascular resistance and increase in cardiac output, with no tachycardia observed. The study concluded that at lower doses CGRP behaves as a pure arteriolar vasodilator, where as at the higher dose CGRP acts a mixed vasodilator. Stephenson, et al. (*Int. J. Cardiol.*, 37:407-414 (1992)) reported administration of CGRP at a rate of 600 ng/min by either a 48-hour continuous IV-infusion or 2-8 hour infusions for two consecutive days. In the continuous infusion therapy, infusion was discontinued after 28 hours in 3 out of the 6 patients due to nausea, diarrhea, and/or severe facial flushing. On the other hand, the pulsed therapy was well tolerated and was observed to improve hemodynamic functions such as left ventricular function. However, unfavorable side effects of tachycardia and neurohumoral response were also observed with the pulsed therapy. Sekhar, et al. (*Am. J. Cardiol.* 67:732-736 (1991) reported administration of CGRP at a rate of 8 ng/kg/min (i.e., 560 ng/min based on a 70 kg subject) by IV infusion for 8 hours. This therapy was observed to have beneficial hemodynamic effects such as decreased pulmonary and systemic arterial pressure, decreased vascular resistance and increased cardiac output. It was also observed that renal blood flow and glomerular filtration were increased during treatment. However, the hemodynamic effects were lost within 30 minutes of stopping CGRP infusion.

Chronic HF is a progressive disease. Therefore, therapies that initially seek to reduce disease progression while increasing the patient's quality of life and relieving symptoms that exacerbate the condition are desirable. It would be far more cost effective and much better for the patient's health if chronic heart failure could be managed and controlled by the routine or controlled release administration of appropriate drug therapy rather than by hospital treatment upon the manifestation of acute symptoms.

SUMMARY OF THE INVENTION

The present invention provides a method for the treatment or prevention of heart failure ("HF") by administering one or more doses of a CGRP formulation in a manner that will treat the conditions underlying HF while minimizing or attenuating deleterious effects commonly associated with CGRP such as nausea, diarrhea, severe facial flushing and intermittent tachycardia. More specifically, this invention provides improved CGRP dosing regimes for patients suffering from or at risk for HF, and a method of treating-HF or delaying the progression of HF into more advanced stages by providing lower dose and longer term administration of CGRP.

Accordingly, one aspect of this invention provides a method of treating HF in a patient comprising administering CGRP to the patient such that circulating plasma levels of CGRP are sufficient to maintain hemodynamic stability, thereby preventing or delaying exacerbation HF symptoms. In prior clinical studies using Stage C and D HF patients, effective circulating plasma levels of CGRP were administered by intravenous infusions ranging between $157\pm26$ pg/mL to $186\pm127$ pg/mL (Anand; et al., 1991 and Shekhar, et al., 1991, supra). However, these doses could only be administered intravenously for about 12-24 hours before unwanted side effects set in and the IV administration had to be discontinued. In contrast, the methods of the present invention administer CGRP by controlled release systems or compositions that maintain circulating plasma levels of CGRP between about $11\pm5$ pg/mL and $186\pm127$ pg/mL for a length of time that is within the capabilities of the particular controlled release delivery system or composition.

In one embodiment, the controlled release composition comprises a biodegradable polymer matrix containing CGRP, wherein CGRP is released from the polymer matrix in situ by diffusion or dissolution from within the polymer matrix and/or by the degradation of the polymeric matrix. The controlled release formulation can also be in film form. In another embodiment, the controlled release formulation comprises solid microparticles formed from the combination of biodegradable, synthetic polymers such as poly(lactic acid) (PLA), poly(glycolic acid) (PGA), and copolymers thereof with CGRP loadings that yield a sustained release over a period of time when administered orally, transmucosally, topically or by injection. In further embodiments, the controlled release formulations comprise CGRP encapsulated in a liposome or CGRP conjugated to a polymer.

The above-described methods and controlled release compositions can further be used for maintenance therapies, preferably using lower doses or dosing rates of CGRP, after the initial therapy is completed.

This invention further provides prophylactic methods of preventing HF in a patient at risk of HF or slowing the progression or symptoms of HF in a patient suffering from HF. For example, another aspect of this invention provides a method of preventing or reducing the risk of occurrence of myocardial infarction in a patient, comprising administering to a human at risk of having a myocardial infarction a controlled release CGRP formulation in an amount effective to prevent or reduce the risk of myocardial infarction.

In all of the above-described methods, the amount of CGRP delivered to the patient depends on the symptoms, stage of HF, degree of severity and/or other medications (e.g., diuretics) being administered to the patient.

This invention further provides a method of augmenting current HF therapies comprising administering CGRP according to the dosing regimes of this invention together with one or more addition drugs for HF, wherein CORP and the additional drug(s) can be administered together, separately and simultaneously, or separately in any order.

This invention further provides a method of counteracting ischemia due to myocardial infarction in a patient, comprising delivering to said patient an amount of CORP effective to provide cardioprotection, reduction in infarction size, reduction in reperfusion injury, symptomatic relief, and/or prevent exacerbation of symptoms, wherein said CGRP is delivered to said patient as a controlled release composition.

Another aspect of this invention comprises a method of improving renal blood flow and glomerular filtration in a patient suffering from diminished renal function, comprising administering CGRP to a patient in need thereof in a manner effective to improve renal blood flow and/or glomerular filtration.

Administering CGRP according to the methods of this invention provides a safer and more effective treatment of acute cardiac ischemia and heart failure compared to current treatments for HF. Given the advantages in cardioprotection, myocardial tissue salvage, cardiac hemodynamic improvement, and renal function provided by CGRP, the methods of this invention have the potential to be powerful frontline weapons in the arsenal of emergency room doctors who are the first to treat patients suffering from myocardial infarction (MI) upon entry into the health care system, and/or an interventional cardiologist who is working to re-establishing blood flow to an ischemic heart using angioplasty or stenting procedures, and/or a cardiologist who is treating mid- to end-stage heart failure patients to provide increased quality of life to terminal patients.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

One aspect of this invention provides improved methods for administering CGRP to a patient having HF in a manner effective to treat or prevent HF. The "patient" can be any living organism, including a warm-blooded mammal such as a human. The treatment according to any of the methods of this invention can be administered on an inpatient such as a hospital or emergency room, or in an outpatient setting such as a hospice or home health care setting or administration by emergency care personnel to a patient having a myocardial infarction. This invention further provides methods of improving hemodynamic functions in a patient with HF by providing improved methods of administering CGRP to the patient in either an inpatient or outpatient setting.

"Treating HF" as used herein refers to treating any one or more of the conditions underlying HF, including, without limitation, decreased cardiac contractility, abnormal diastolic compliance, reduced stroke volume, pulmonary congestion, decreased cardiac output, and other diminished hemodynamic functions, while minimizing or attenuating deleterious effects that may be associated with the long-term administration of CGRP such as nausea, diarrhea, severe facial flushing and intermittent tachycardia. "Treating HF" also includes relieving or attenuating symptoms associated with HF.

This invention also provides a method of improving the quality of life in a patient with HF. "Quality of life" refers to one or more of a person's ability to walk, climb stairs, do errands, work around the house, participate in recreational activities, and/or not requiring frequent rest intermittently during activities, and/or the absence of sleeping problems or shortness of breath.

For purposes of this invention, a "patient having HF" refers to a person having Stage B, Stage C, or Stage D heart failure as classified in the American College of Cardiology Guidelines for the Evaluation and Management of Chronic Heart Failure in the Adult. While the American College of Cardiology Guidelines excluded HF in children, for purposes of this invention the methods are to be considered applicable to any patient, regardless of age.

More specifically, this invention provides improved methods for providing effective amounts of CGRP for treating or preventing HF and/or for improving renal function in a patient. In the treatment of HF according to this invention, compositions comprising CGRP alone or in combination with other drugs or therapies will be formulated, dosed, and administered in a fashion consistent with good medical practice. It is to be understood that the actual dose will depend on the particular factors of each case. Generally, the dosage required to provide an effective amount of CGRP or a pharmaceutically acceptable salt thereof is within the ranges disclosed herein and can be adjusted by one of ordinary skill in the art. The dosage will vary depending on the clinical condition of the individual patient (especially the side effects of treatment with CGRP alone or in combination with other therapeutics), the age, health, physical condition, sex, diet and medical condition of the patient, the severity (i.e., stage) of heart failure, the route of administration, the site of delivery of CGRP, the type of drug delivery system that is used, whether CGRP is administered as part of a drug combination, the scheduling of administration, and other factors known to practitioners. Thus, while individual needs may vary, determination of optimal ranges for effective amounts of CGRP (alone or in combination with other drugs) within the ranged disclosed herein is within the expertise of those skilled in the art. Accordingly, "effective amounts" of each component for purposes herein, are determined by such considerations and are amounts that improve one or more hemodynamic functions and/or ameliorate on or more deleterious conditions in HF patients and/or improve the quality of life in HF patients and/or improve renal function.

The term "hemodynamic functions" includes, but is not limited to, heart rate, right atrial pressure, pulmonary artery pressure, pulmonary artery wedge pressure, systemic arterial pressure, cardiac output (i.e., cardiac index), stroke volume index, pulmonary vascular resistance, and systemic vascular resistance.

The term "improved hemodynamic functions" includes, but is not limited to, increased cardiac output, decreased pulmonary artery wedge pressure, decreased pulmonary vascular resistance, and decreased systemic vascular resistance, increased cardiac contractility, normal diastolic compliance, increased stroke volume and reduced pulmonary congestion.

The term "afterload" refers to the resistance that the heart has to overcome during every beat to send blood into the aorta. This resistive force includes vasoactivity and blood viscosity.

The term "cardiac index" (CI) refers to amount of blood pumped by the heart per minute per meter squared of body surface area.

The term "cardiac output" (CO) refers to the volume of blood pumped by the heart in one minute. Increased cardiac output can indicate a high circulating volume. Decreased cardiac output indicates a decrease in circulating volume or a decrease in the strength of ventricular contraction.

The term "central venous pressure" (CVP) refers to readings that are used to approximate the Right Ventricular End Diastolic Pressure (RVEDP). The RVEDP assesses right ventricular function and general fluid status. Low CVP values typically reflect hypovolemia or decreased venous return, and high CVP values reflect overhydration, increased venous return or right-sided cardiac failure.

The term "change in heart rate" refers to a condition that indicates tachycardia or increased workload.

The term "dyspnea" means shortness of breath. Dyspnea is a primary clinical endpoint to address efficacy in heart failure treatments.

The term "left ventricular stroke index" (LVSI) refers to the difference in contractile position of the left ventricle from the resting position to the point of maximum contraction.

The term "mean arterial pressure" (MAP) refers to changes in the relationship between cardiac output (CO) and systemic vascular resistance (SVR) and reflects the arterial pressure in the vessels perfusing the organs. A low MAP indicates decreased blood flow through the organs, and a high MAP indicates an increased cardiac workload.

The term "neurohormone release" refers to a response by the kidneys to increase renal blood flow by releasing the vasoconstricting neurohormones norepinephrine, epinephrine, and rennin. These hormones act to constrict peripheral vasculature adversely affecting the PVR.

The term "preload" refers to the combination of pulmonary blood filling the atria and the stretching of myocardial fibers. Preload is regulated by the variability in intravascular volume. A reduction in volume decreases preload, whereas an increase in volume increases preload, mean arterial pressure (MP) and stroke index (SI). Preload occurs during diastole.

The term "pulmonary artery pressure" (PA pressure) refers to blood pressure in the pulmonary artery. Increased pulmonary artery pressure may indicate a left-to-right cardiac shunt, pulmonary artery hypertension, COPD, emphysema, pulmonary embolus, pulmonary edema, or left ventricular failure.

The term "pulmonary capillary wedge pressure" (PCWP or PAWP) refers to a pressure are used to approximate LVEDP (left ventricular end diastolic pressure). High PCWP may indicate left ventricle failure, mitral valve pathology, cardiac insufficiency, and/or cardiac compression post hemorrhage. PCWP is a primary clinical endpoint to address efficacy in heart failure treatments.

The term "pulmonary vascular resistance" (PVR) refers to the measurement of resistance or the impediment of the pulmonary vascular bed to blood flow. An increased PVR is caused by pulmonary vascular disease, pulmonary embolism, pulmonary vasculitis, or hypoxia. A decreased PVR is caused by medications such as calcium channel blockers, aminophylline or isoproterenol, or by the delivery of $O_2$.

The term "renal blood flow" (RBF) refers to the measurement of blood flow into the kidneys. Twenty percent of cardiac output passes through the kidneys, which compromise less than 1% of body weight. Increased renal blood flow is proportional to increased renal function and urine output.

The term "renal glomerular filtration" (RBF) refers to the first step in urine formation as protein-free ultrafiltrate plasma crosses the walls of the glomerular capillaries increased renal blood flow increases flow of plasma across the glomeruli, increasing urine output.

The term "right ventricular pressure" (RV Pressure) refers to a direct measurement that indicates right ventricular function and general fluid status. High RV pressure may indicate pulmonary hypertension, right ventricle failure, or congestive heart failure.

The terms "stroke index" or "stroke volume index" (SI or SVI) are used interchangeably and refer to the amount of blood ejected from the heart in one cardiac cycle, relative to Body Surface Area (BSA). SVI is measured in milliliters per meter squared per beat. An increased SVI can be indicative of early septic shock, hyperthermia or hypervolemia, or can be caused by medications such as dopamine, Dobutamine or Digitalis. A decreased SVI can be caused by CHF, late septic shock, beta-blockers or an MI.

The term "stroke volume" (SV) refers to the amount of blood pumped by the heart per cardiac cycle, and is measured in milliliters per beat. A decreased SV may indicate impaired cardiac contractility or valve dysfunction and may result in heart failure. An increased SV can be caused by an increase in circulating volume or an increase in inotropy.

The term "systemic vascular resistance" (SVR refers to the measurement of resistance or impediment of the systemic vascular bed to blood flow. An increase in SVR can be caused by vasoconstrictors, hypovolemia or late septic shock. A decrease in SVR can be caused by early septic shock, vasodilators, morphine, nitrates or hypercarbia.

A "microgram" (µg) is 1 millionth of a gram, i.e., $10^{-6}$ grams.

A "nanogram" (ng) is 1 billionth of a gram, i.e., $10^{-9}$ grams.

A "picogram" pg) is 1 trillionth of a gram, i.e., $10^{-12}$ grams.

Table 1 provides normal values for the above-described hemodynamic parameters.

TABLE 1

| Hemodynamic Parameter | Normal Value |
| --- | --- |
| Blood Pressure Systolic (SBP) | 90-140 mm Hg |
| Diastolic (DBP) | 60-90 mm Hg |
| Mean Arterial Pressure (MAP) | 70-100 mm Hg |

TABLE 1-continued

| Hemodynamic Parameter | Normal Value |
| --- | --- |
| Cardiac Index (CI) | 2.5-4 L/min/m$^2$ |
| Cardiac Output (CO) | 4-8 L/min |
| Central Venous Pressure (CVP) | 2-6 mm Hg |
| Pulmonary Artery Pressure (PA) | Systolic: 20-30 mm Hg (PAS) |
| | Diastolic: 8-12 mm Hg (PAD) |
| | Mean: 25 mm Hg (PAM) |
| Pulmonary Capillary Wedge Pressure (PWCP) | 4-12 mm Hg |
| Pulmonary Vascular Resistance (PVR) | 37-250 dynes/sec/cm$^3$ |
| Right Ventricular Pressure (RV) | Systolic-20-30 mm Hg |
| | Diastolic 0-5 mm Hg |
| Stroke Index (SI) | 25-45 mL/m$^2$ |
| Systemic Vascular Resistance (SVR) | 800-1200 dynes/sec/cm$^3$ |

Various sources of CGRP may be used in the methods of this invention. For example, synthetic CGRP may be obtained using an automatic peptide synthesizer according to well known methods. One method for synthesizing the CGRP is the well known Merrifield method (see, Merrifield, R. B., *J. Am. Chem. Soc.* 85:2149 (1963) and Merrifield, R. B., *Science,* 232:341 (1986), which are specifically incorporated herein by reference). Human CGRP also may be obtained from commercial sources, such as Peninsula Laboratory (Belmont, Calif.), Bachem Biosciences, Inc. (King of Prussia, Pa.) and Sigma Chemicals (St. Louis, Mo.). Commercial grade human CGRP is not marketed for human use (since this grade is not GMP/GLP grade); therefore, commercially available human CGRP may be used in the present invention only if it is purified and sterilized so that it is fit for human use. Genetically engineered human CGRP can also be used in the present invention. Similar results also could be achieved using a CGRP analogue or an analogue based on the CGRP "receptor structure." These include peptide-based analogues, as well as peptide-mimetic analogues. Accordingly, analogs that function similarly to CGRP are considered to be equivalents of CGRP for purposes of this invention. Animal-derived CGRP is biologically active and thus could be used in the present invention; however, as a practical matter, animal-derived CGRP presents allergy and autoimmune problems and therefore is preferably avoided.

Other forms of CGRP that are suitable for use in the methods of this invention are pharmaceutically acceptable prodrugs of CGRP. A "pharmaceutically acceptable prodrug" is a compound that may be converted under physiological conditions or by solvolysis to the specified compound or to a pharmaceutically acceptable salt of such compound. Prodrugs of CGRP may be identified using routine techniques known in the art. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino-groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities. Other examples of such prodrug derivatives are described in a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5. "Design and Application of Prodrugs", by H. Bundgaard p. 113-191 (1991); c) H. Bundgaard, Advanced Drug Delivery Reviews, 8:1-38 (1992); d) H. Bundgaard, et al., *J. Pharmaceutical Sciences,* 77:285 (1988); and e) N. Kakeya, et al., *Chem. Pharm. Bull.,* 32:692 (1984), each of which is specifically incorporated herein by reference.

When administered in controlled dosages, CGRP has pronounced cardiovascular benefits, including vasodilation, ischemic cardioprotection, reduction in infarction size due to heart attack, inhibition of platelet aggregation and smooth muscle cell proliferation to potentially reduce the incidence of restenosis, increased renal function, and overall increased efficiency of cardiovascular functions. CGRP also plays a role in regulating inotropy, chronotropy, microvascular permeability, vascular tone, and angiogenesis.

As stated, CGRP has significant advantages over conventional drug treatments. First, CGRP does not produce the potentially dangerous side effects, toxicity and tolerance associated with conventional cardiovascular drugs such as nitroglycerin, Dobutamine and Natrecor. In fact, CGRP has been reported to down-regulate immune response via inhibition of cytokine release and has been safely administered to immunosuppressed subjects without the induction of sensitivity. Second, since CGRP possesses multiple hemodynamic benefits, it potentially reduces or eliminates the need for drug cocktails to maintain specific hemodynamic functions. Third, more than 20 years of research on the potency, safety and efficacy of the drug in animals and humans have demonstrated the cardiovascular benefits of CGRP and have shown that CGRP exhibits virtually no side effects or tolerance when administered systemically.

In general, there are four goals in treating HF patients: (1) treating the symptoms, (2) slowing the progression of cardiac dysfunction, (3) decreasing length of hospital stay, and (4) increasing the time between hospitalization, all while minimizing health care costs. It is believed that the methods for the treatment or prophylaxis of HF according to this invention will achieve one or more of these goals.

In order to use CGRP for the therapeutic treatment (including prophylactic treatment) of mammals including humans according to the methods of this invention, it is normally formulated in accordance with standard pharmaceutical practice as a pharmaceutical composition. According to this aspect of the invention there is provided a pharmaceutical composition comprising CGRP in association with a pharmaceutically acceptable diluent or carrier, wherein the CGRP is present in an amount for effective treating or preventing HF and/or for improving renal function.

CGRP can be administered to a patient by any available and effective delivery system including, but not limited to, parenteral, transdermal, intranasal, sublingual, transmucosal, intra-arterial, or intradermal modes of administration in dosage unit formulations containing conventional nontoxic pharmaceutically acceptable carriers, adjuvants, and vehicles as desired, such as a depot or a controlled release formulation.

For example, CGRP or a pharmaceutically acceptable formulation thereof may be formulated for parenteral administration, e.g., for intravenous, subcutaneous, or intramuscular injection. For an injectable formulation, a dose of CGRP may be combined with a sterile aqueous solution which is preferably isotonic with the blood of the patient. Such a formulation may be prepared by dissolving a solid active ingredient in water containing physiologically-compatible substances such as sodium chloride, glycine, and the like, and having a buffered pH compatible with physiological conditions so as to produce an aqueous solution, and then rendering the solution sterile by, methods known in the art. The formulations may be present in unit or multi-dose containers, such as sealed ampules or vials. The formulation may be delivered by any mode of injection, including, without limitation, epifascial, intracutaneous, intramuscular, intravascular, intravenous, parenchymatous, subcutaneous, oral or nasal preparations (see, for example, U.S. Pat. No. 5,958,877, which is specifically incorporated herein by reference).

Pharmaceutical compositions may also be in the form of a sterile injectable aqueous or oily suspension, which may be formulated according to known procedures using one or more appropriate dispersing or wetting agents and suspending agents. A sterile injectable preparation may also be a sterile injectable solution or suspension in a non-toxic parenterally-acceptable diluent or solvent, for example a solution in 1,3-butanediol.

In any of the embodiments of this invention, CGRP is optionally conjugated to a biocompatible, biodegradable polymer to form a conjugate. As used herein, the term "conjugate" refers to a CGRP molecule covalently or noncovalently coupled to one or more polymers. Examples of polymers include, but are not limited to, biological polymers (e.g., polysaccharides, polyamides, pharmacologically inert nucleotide components, etc.), derivatives of biological polymers, and non-biological polymers. Specific examples include, are not limited to, poly(alkylene glycols such as poly(ethylene glycol) (PEG), poly-lactic acid (ALA), poly-glycolic acid, poly(ε-caprolactone), poly(β-hydroxybutyrate), poly(β-hydroxyvalerate), polydioxanone, poly(malic acid), poly(tartronic acid), poly(ortho esters), polyanhydrides, polycyanoacrylates, poly(phosphoesters), polyphosphazenes, hyaluronidate, polysulfones, polyacrylamides, polymethacrylate, chimeric recombinant elastin-silk protein (Protein Polymers, Inc.) and collagen (Matrix Pharmaceuticals, Inc) (for detailed discussion of the above mentioned polymers, see, Park, K. et al. (1993) Biodegradable Hydrogels for Drug Delivery. Technomic Publishing Co., Inc., Lancaster, Pa.). The polymers noted above can optionally be crosslinked to modify the utility thereof, such as to render the compounds more or less water soluble. Numerous crosslinking agents are useful, including diols and higher polyols, polyamines, polycarboxylic acids, polyisocyanates and the like.

CGRP can be conjugated to any of the above-described polymers using conventional methods known to those skilled in the art, wherein the conjugation is performed under conditions which do not substantially reduce the pharmacological activity of CGRP. For example, CGRP can be covalently coupled to the polymer directly through reaction of a reactive group on the CGRP with a reactive group of the polymer. The term "reactive group" refers to a chemical moiety which is attached to CGRP or the polymer or bonds in the polymer which participate in the chemical reaction between the components involved, i.e., CGRP and the polymer. Examples of reactive groups include without limitation hydroxyl, carboxyl, amine, amide, carbon-carbon double and triple bonds, epoxy groups, halogen or other leaving groups and the like.

Alternatively, CGRP can be coupled to the polymer through a linking group. The term "linking group" is not limited to molecules per se, and refers to compounds, molecules and molecular fragments that can react with the polymer, monomers and CGRP to attach CGRP to the polymer. As such, the linking groups include compounds and the like with more than one reactive group, preferably two or three reactive groups.

Parenteral Administration

According to one embodiment, this invention provides a method of treating BF in a patient comprising administering CGRP or a pharmaceutically acceptable composition thereof to the patient at a rate between about 50 and 500 ng/min for a time between 30 minutes and 8 hours per day for as many days as needed to provide symptomatic relief, prevent exacerbation of symptoms, and/or prevent and/or delay progression of the disease state of heart failure in said patient. For example, CGRP may be continuously or intermittently administered for a period of time between about 24 and 48 hours, or as a bolus dose. If CGRP is administered two or more times intermittently each day, lower doses, e.g., 0.8 to 10 ng/min can be administered.

Treatment is continued as needed to provide symptomatic relief, prevent exacerbation of symptoms, and/or prevent and/or delay progression of the disease state of heart failure in said patient, or until it is no longer well tolerated by the patient, or until a physician terminates treatment. For example, a physician may monitor one or more symptoms of HF, renal blood flow, glomerular filtration rates, and/or serum levels of urea and creatinine in a patient being treated with CGRP according to this invention and, upon observing attenuation of one or more symptoms of HF for a period of time, conclude that the patient can sustain the positive effects of the above-described treatment without further administration of CGRP for a period of time. If necessary, the patient may then return at a later point in time for additional treatment as needed.

According to another embodiment, this invention provides a method of treating HF in a patient comprising administering CGRP to the patient at a rate between about 500 and 600 ng/min for period between about 8 hours per day for at least three consecutive days or several times per week as needed to provide symptomatic relief, prevent exacerbation of symptoms, and/or prevent and/or delay progression of the disease state of heart failure in the patient. This treatment may be provided as outpatient therapy to prevent exacerbation of the heart failure and to enhance the quality of life in the patient.

As used herein, "day" means a 24-hour period. Thus, for example, "for at least three consecutive days" means for at least a 72-hour period. During or after the treatment, a physician may monitor one or more symptoms of HF, renal blood flow, glomerular filtration rates, and/or serum levels of urea or creatinine in the patient and, upon observing an improvement in one or more of the parameters for a period of time, conclude that the patient can sustain the positive effects of the treatment without further administration of CGRP for a period of time.

According to another embodiment, this invention provides a method of treating HF in a patient comprising administering CGRP to the patient at a rate between about 50 and 400 ng/min over a period of up to 8 hours per day for each day of hospitalization of the patient or as needed. In certain cases the patient may require higher doses, for example up to 2 μg/min over the same time period.

Once treatment with CGRP according to any of the methods of this invention has achieved the desired results, e.g., symptomatic relief, prevent exacerbation of symptoms, and/or prevent and/or delay progression of the disease state of heart failure, the patient can then receive maintenance therapy if desired. For example, a lower dose of CGRP, e.g., less than 10 ng/min, can be administered to the patient for maintenance therapy by any suitable route including, but not limited to, injection, intravenous administration, etc. In one embodiment, the delivery regime can be designed to deliver between CGRP at a rate between about 0.8 to 10 ng/min for a desired period of time, such as over a period of 3, 6 or 9 months.

Because CGRP therapy according to any of the methods of this invention prevents further damage from ischemic injury and promotes the healing process, it can also be used to delay or preclude further exacerbation of a heart condition into a more serious and progressive diseases such as HF. Thus, each of the above-described methods may also be used as a prophylactic treatment to prevent or slow the progression of early stages of HF to more advanced stages. That is, once treatment with CGRP according to any of the methods of this invention has achieved the desired results, the patient can optionally receive maintenance therapy thereafter. For example, one embodiment of this invention for providing maintenance therapy to a patient with a heart, condition comprises providing a lower dose of CGRP, e.g., less than 10 ng/min, to the patient for maintenance therapy by any suitable route including, but not limited to, injection, intravenous administration, controlled release administration, etc. In one embodiment, the delivery system can be designed to deliver between CGRP at a rate between about 0.8 to 10 ng/min for a desired period of time, such as over a period of 3, 6 or 9 months. In an alternative embodiment, the patient can receive long-term, low dose, maintenance administration of CGRP from a controlled release formulation.

In addition, it is known that a patient that has suffered a myocardial infarction (MI) will likely suffer another MI in the future. Thus, a patient having an MI can be treated with an initial dose of CGRP according to any of the methods of this invention until one or more symptoms of HF has diminished, and subsequently can be put on a CGRP maintenance dosing regime. The maintenance regime can also be given to a post-MI patient that was initially treated for MI by means other than CGRP, and can also be used for HF patients that have not yet suffered an MI as a means to slow the progression of HF into the more advanced stages or to prevent or reduce the risk of MI in patients with advanced HF.

This invention further provides methods for improving renal function in a patient suffering from diminished renal function comprising administering CGRP according to any of the above-describe dosing regimes for treating HF. As used herein, the term "improved renal function" includes increased glomerular filtration, increased renal blood flow and decreased serum levels of urea and creatinine.

If necessary, CGRP can be administered according to the methods of this invention either alone or in combination with at least one other agent including, but not limited to, anti-proliferative agents, anti-clotting agents, vasodilators, diuretics, beta-blockers calcium ion channel blockers, blood thinners, cardiotonics, ACE inhibitors, anti-inflammatories, antioxidants, and/or gene therapeutics. When used in combination with other agents, CGRP and the agent can be administered separately (either simultaneously or separately in any order) or in admixture. In one embodiment, when CGRP and at least one other agent are administered as separate components, they are administered to the patient at about the same time. "About the same time" means that within about thirty minutes of administering one compound (e.g., CGRP) to the patient, the other compound (e.g., an anti-proliferative or anti-clotting agent) is administered to the patient. "About the same time" also includes concomitant or simultaneous administration of the compounds.

Controlled Release Administration

Another aspect of this invention provides methods of treating HF and/or renal failure by delivering CGRP to a patient as a controlled releases formulation. As used herein, the term "controlled" or "sustained" release of CGRP includes continuous or discontinuous, linear or non-linear release of CGRP. There are many advantages for a controlled release formulation of CGRP. Among these are the convenience of a single injection for the patient, avoidance of peaks and valleys in systemic CGRP concentration which can be associated with repeated injections, the potential to reduce the overall dosage of CGRP, delayed progression of HF, cardioprotection, and the potential to enhance the pharmacological effects of CGRP. A lower, sustained dose can also prevent adverse affects that are occasionally observed with infusion therapy. In addition to significantly reducing the cost of care, controlled release drug therapy can free the patient from repeated treatment or hospitalization thus offering the patient greater flexibility and improving patient compliance. A controlled release formulation of CGRP also provides an opportunity to use CGRP in a manner not previously exploited or considered, such as a maintenance therapeutic for patients that have suffered an MI or in patients at high risk of suffering an MI, such as Stage B, C and D heart failure patients.

1. Controlled Release Implant

One embodiment of a controlled release composition of this invention comprises suitable for use in treating or preventing HF comprises a flowable composition that forms a biodegradable implant comprising CGRP in situ. This invention further comprises a kit that includes the flowable composition. The flowable composition comprises a biodegradable, biocompatible thermoplastic polymer or copolymer in combination with a suitable polar solvent and CGRP. The thermoplastic polymers or copolymers are substantially insoluble in water and body fluid and are biodegradable and/or bioerodible within the body of an animal. The flowable composition is administered for example as a liquid or gel to a tissue or bodily fluid wherein the implant (i.e., a polymer matrix) is formed in situ, and CGRP is subsequently released from the matrix by diffusion or dissolution from within the polymer matrix and/or by the degradation of the polymeric matrix. The composition is biocompatible and the polymer matrix does not cause substantial tissue irritation or necrosis at the implant site. Examples of biocompatible, biodegradable controlled release polymer formulations suitable for purposes of this invention are provided in U.S. Pat. Nos. RE 37,950 E, 6,143,314 and 6,582,080 B2, which are specifically incorporated herein by reference.

More specifically, a flowable thermoplastic polymeric composition of this invention comprises a thermoplastic polymer or copolymer dissolved in a pharmaceutically-acceptable organic solvent that is miscible to dispersible in an aqueous medium to provide a polymeric solution, and CGRP or a CGRP conjugate either dissolved to form a homogeneous solution or dispersed to form a suspension or a dispersion of CGRP within the polymeric solution. When the polymer solution is placed in an aqueous environment, such as a bodily tissue or fluid which typically surround tissues or organs in an organism, the organic solvent dissipates or disperses into the aqueous or body fluid. Concurrently, the polymer precipitates or coagulates to form a solid matrix or implant and CGRP becomes trapped or encapsulated within the polymeric matrix as the implant solidifies. Once the solid implant is formed, CGRP is released from the solid matrix by diffusion or dissolution from within the polymeric matrix and/or by the degradation of the polymeric matrix.

Preferably, the flowable composition is a liquid, gel, paste or putty suitable for injection in a patient. As used herein, "flowable" refers to the ability of the composition to be administered by any suitable means into the body of a patient. For example, the composition can be injected into a specific site in the patient with the use of a syringe and puncture needle or placed into accessible tissue sites through a cannula. The ability of the composition to be injected into a patient will typically depend upon the viscosity of the composition. The composition will therefore have a suitable viscosity such that the composition can be forced through the medium (e.g., syringe) into the body of a patient. As used herein, a "liquid" is a substance that undergoes continuous deformation under a shearing stress (Concise Chemical and Technical Dictionary, $4^{th}$ Enlarged Ed., Chemical Publishing Co., Inc., p. 707, N.Y., N.Y. (1986)). The term "gel" refers a substance having a gelatinous, jelly-like, or colloidal property (Concise Chemical and Technical Dictionary, $4^{th}$ Enlarged Ed., Chemical Publishing Co., Inc., p. 567, N.Y., N.Y. (1986)).

The term "biodegradable" means that the polymer matrix will degrade over time, for example by the action of enzymes, by hydrolytic action and/or by other similar mechanisms in the patient's body. By "bioerodible," it is meant that the polymer matrix will erode or degrade over time due, at least in part, to contact with substances found in the surrounding tissue fluids or cellular action. By "bioabsorbable" it is meant that the polymer matrix will be broken down and absorbed within the human body, for example, by a cell or tissue. "Biocompatible" means that the polymer, the solvent and the resulting polymer matrix will not elicit an adverse biologic response in the patient.

A thermoplastic composition is provided in which a biodegradable polymer and CGRP are dissolved in a biocompatible solvent to form a flowable composition, which can then be administered, for example, via a syringe and puncture needle or a catheter. Any suitable biodegradable, bioabsorbable, and/or bioerodible thermoplastic polymer can be employed, provided the biodegradable thermoplastic polymer is at least substantially insoluble in aqueous medium or body fluid. Suitable biodegradable thermoplastic polymers are disclosed, e.g., in U.S. Pat. Nos. 5,324,519; 4,938,763; 5,702,716; 5,744,153; and 5,990,194, each of which is specifically incorporated herein by reference. The thermoplastic polymers can be made form a variety of monomers which form linear or branched polymer chains or monomeric units joined together by linking groups such as esters, amides urethanes, etc. According to one embodiment, some fraction of one of these starting monomers will be at least trifunctional, and provides at lest some branching of the resulting polymer chain. Examples of suitable biodegradable polymers include, but are not limited to, polylactides, polyglycolides, polycaprolactones, polyanhydrides, polyamides, polyorthoesters, polyurethanes, polyesteramides, polydioxanones, polyacetals, polyketals, polycarbonates, polyorthocarbonates, polyphosphazenes, polyhydroxybutyrates, polyhydroxyvalerates, polyalkylene oxalates, polyacrylates, polyalkylene succinates, poly(malic acid), poly(amino acids) and copolymers, terpolymers, cellulose diacetate and ethylene vinyl alcohol copolymers, and combinations thereof.

The type, molecular weight, and amount of biodegradable thermoplastic polymer present in the composition will typically depend upon the desired properties of the controlled release implant. For example, the type, molecular weight, and amount of biodegradable thermoplastic polymer can influence the length of time in which CGRP is released from the controlled release implant. Specifically, in one embodiment of the present invention, the composition can be used to formulate a one month delivery system of CGRP. In such an embodiment, the biodegradable thermoplastic polymer can preferably be 50/50 poly (DL-lactide-co-glycolide), can be present in about 30 wt. % to about 40 wt. % of the composition, and can have an average molecular weight of about 12,000 to about 45,000. Alternatively, in another embodiment the composition can be used to formulate a three month delivery system of CGRP. In such an embodiment, the biodegradable thermoplastic polyester can preferably be 75/25 poly (DL-lactide-co-glycolide), can be present in about 40 wt. % to about 50 wt. % of the composition, and can have an average molecular weight of about 15,000 to about 24,000.

The molecular weight of the polymer used in the present invention can affect the rate of CGRP release in situ from the implant. As the molecular weight of the polymer increases, the rate of CGRP release from the system decreases. This phenomenon can be advantageously used in the formulation of systems for the controlled release of CGRP. For relatively quick release of CGRP, low molecular weight polymers can be chosen to provide the desired release rate. For release of a CGRP over a relatively long period of time, a higher polymer molecular weight can be chosen. Accordingly, a polymer system can be produced with an optimum polymer molecular weight range for the release of CGRP over a selected length of time. The molecular weight of a polymer can be varied by any of a variety of methods known to persons skilled in the art.

The particular biocompatible polymer employed is not critical and is selected relative to the viscosity of the resulting polymer solution, the solubility of the biocompatible polymer in the biocompatible solvent, the desired release rate, and the like. Such factors are well known to persons skilled in the art. The biodegradable thermoplastic polyester is preferably present in about 30 wt. % to about 50 wt. % of the flowable composition. Preferably, the biodegradable thermoplastic polyester has an average molecular weight of about 12,000 to about 45,000 and more preferably from about 15,000 to about 30,000.

The concentration of the polymer dissolved in the various solvents will differ depending upon the type of polymer and its molecular weight, and these factors can be varied to obtain optimum injection efficiency. CGRP is added to the polymer solution where it is either dissolved to form a homogenous solution or dispersed to form a suspension or a dispersion of drug within the polymeric solution.

Suitable organic solvents for preparing the thermoplastic polymer composition are those that are biocompatible, pharmaceutically acceptable, and able to diffuse into in aqueous or body fluids so that the flowable composition coagulates or solidifies. The organic solvent is capable of diffusing, dispersing, or leaching from the composition in situ into aqueous tissue or body fluid of the implant site. Examples of suitable solvents include substituted heterocyclic compounds such as N-methyl-2-pyrrolidone and 2 pyrrolidone; esters of carbonic acid and alkyl alcohols such as propylene carbonate, ethylene carbonate and dimethyl carbonate; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; alcohols such as solketal, glycerol formal, and glycofurol; dialkylamides such as dimethylformamide, dimethylacetamide; dimethylsulfoxide (DMSO) and dimethylsulfone; tetrahydrofuran; lactones such as ϵ-caprolactone and butyrolactone; cyclic alkyl amides such as caprolactam; aromatic amides such as N,N-dimethylm-toluamide and 1-dodecylazacycloheptan-2-one; and mixtures and combinations thereof. Preferred solvents include polar aprotic solvents such as N-methyl-2-pyrrolidone, 2-pyrrolidone, N-dimethyl formamide, dimethylsulfoxide, caprolactam, triacetin, ethyl lactate, propylene carbonate, solketal, glycerol formal, glycofurol, or any combination thereof.

The solvent can be present in any suitable amount, provided the solvent is miscible to dispersible in aqueous medium or body fluid. The type and amount of biocompatible solvent present in the composition will typically depend upon the desired properties of the controlled release implant. For example, the type and amount of biocompatible solvent can influence the length of time in which the CGRP is released from the controlled release polymer matrix. Preferably, the solvent is present in about 45-70 wt. % of the polymeric composition. Specifically, in one embodiment of the present invention, the composition can be used to formulate a one month delivery system of CGRP. In such an embodiment, the biocompatible solvent can preferably be N-methyl-2-pyrrolidone and can preferably present in about 60 wt. % to about 70 wt. % of the composition. Alternatively, in another embodiment of the present invention, the composition can be used to formulate a three month delivery system of CGRP. In such an embodiment, the biocompatible solvent can preferably be N-methyl-2-pyrrolidone and can preferably present in about 50 wt. % to about 60 wt. % of the composition.

The solubility of the biodegradable thermoplastic polymers in the various solvents will differ depending upon their crystallinity, their hydrophilicity, hydrogen-bonding, bonding, and molecular weight. Thus, not all of the biodegradable thermoplastic polymers will be soluble in the same solvent, and each biodegradable thermoplastic polymer or copolymer will have its appropriate solvent.

A method for forming a flowable polymeric composition includes mixing, in any order, a biodegradable thermoplastic polyester, a biocompatible solvent, and CGRP. These ingredients, their properties, and preferred amounts are as disclosed above. The mixing is performed for a sufficient period of time effective to form the flowable composition for use as a controlled release implant. Preferably, the biocompatible thermoplastic polyester and the biocompatible solvent are mixed together to form a mixture and the mixture is then combined with CGRP to form the flowable composition. If necessary, gentle heating and stirring can be used to effect dissolution of the biocompatible polymer into the biocompatible solvent.

The amount of CGRP incorporated into the polymeric composition depends upon several factors, including but not limited to the desired release profile, the concentration of CGRP required for a biological effect, and the length of time that CGRP has to be released for effective treatment. There is no critical upper limit on the amount of CGRP incorporated into the polymer solution except for that of an acceptable solution or dispersion viscosity for injection through a syringe needle. The lower limit of CGRP incorporated into the delivery system is dependent simply upon the activity of the CGRP and the length of time needed for treatment.

The release of CGRP from the solid polymer matrices (implants) will follow the same general rules for release of a drug from a monolithic polymeric device. The release of CGRP can be affected by the size of the implant (i.e., the amount of polymer composition administered to the patient), the loading of CGRP within the implant, the permeability factors involving CGRP and the particular polymer, and the degradation of the polymer. Depending upon the amount of CGRP selected for delivery, the above parameters can be adjusted by one skilled in the art of drug delivery to give the desired rate and duration of release. Thus, the flowable composition can be designed to produce an implant that will release CGRP over a targeted period from days to months.

The amount of flowable composition administered will typically depend upon the desired properties of the controlled release implant. For example, the amount of flowable composition can influence the length of time in which CGRP is released from the controlled release implant.

It is desirable with any of the controlled release systems or formulations described herein that CGRP is delivered to the patient at a rate and in an amount that will achieve blood plasma levels necessary to provide symptomatic relief, e.g., by attenuating one or more symptoms of HF. The following are examples of minimum and maximum IV infusion rates, cumulative daily dose and plasma levels required to bring about the full range of hemodynamic benefits that CGRP induces without any serious side effects in hemodynamically compromised patients. Minimal and transient facial flushing may be observed, but dosages are very well tolerated in IV infusions.

1. Minimum infusion rate and daily dose delivered to cause attenuation of one or more symptoms of HF for a patient weighing 70 kg: 0.0008 µg/kg/min×70 kg×1440 minutes 80.64 µg/day.

2. Maximum infusion rate and daily dose delivered to cause attenuation of one or more symptoms of HF for a patient weighing 70 kg: 0.016 µg/kg/min×70 kg×1440 minutes 1.6 mg/day.

It is well within the skill of persons skilled in the art to determine the amount of CGRP to be loaded into a particular drug delivery system to provide the desired steady state plasma levels of CGRP as described herein to provide relief of one or more symptoms of HF or to improve one or more hemodynamic properties according to the methods of this invention.

The following is an example of the amount of CGRP to include in a transdermal delivery system that will deliver CGRP across the skin at a rate suitable to maintain a steady state plasma level of 157±26 µg/mL, which has been found to produce profoundly beneficial hemodynamic responses including increased cardiac output, decreased ventricular filling pressures, pulmonary and systemic arterial pressures, vascular resistance, increased glomerular filtration, and renal blood flow. If it is assumed that a transdermal delivery system can deliver 25% of the loaded CGRP across the skin, then in order to deliver a total drug load similar to that delivered by an IV dose of 560 ng/min (0.008 µg/kg/min) over 8-24 hours (i.e., delivery of 288-806 µg CGRP) the total drug load required for the transdermal delivery system would be approximately 1.152-3.456 mg. Polymer matrix systems capable of delivering 100% of the drug at a rate suitable to maintain similar steady state plasma levels would require a total drug load four times less than transdermal systems, i.e., 0.288-0.806 mg. Peak plasma levels of CGRP at 157±26 pg/ml are obtained in the first 60 minutes. In a preferred embodiment the peak level is maintained for 8-24 hours.

Tables 2 and 3 show examples of the amount of CGRP to be added to a flowable composition and the corresponding injection volumes in order to produce implants that will provide the indicated delivery rates over 7, 30, 60, 90, 120 or 180 days and maintain steady state plasma levels of CGRP up to 157±26 pg/mL. In Tables 2 and 3, delivery rates and CGRP loads are provided for compositions that will produce implants in situ comprising 5 wt. % and 15 wt. % CGRP, respectively.

TABLE 2

Thermoplastic polymer compositions comprising 5% CGRP

| Delivery Rate | | Duration of release (Days) | | | | |
|---|---|---|---|---|---|---|
| | | 7 | 30 | 90 | 120 | 180 |
| 0.0008 μg/kg/min | Drug Load (mg) | 0.56 | 2.42 | 7.26 | 9.68 | 14.52 |
| | Injection (cc) | 0.01 | 0.05 | 0.15 | 0.19 | 0.29 |
| 0.0032 μg/kg/min | Drug Load (mg) | 2.26 | 9.69 | 29.07 | 38.76 | 58.14 |
| | Injection (cc) | 0.04 | 0.19 | 0.58 | 0.77 | 1.16 |
| 0.008 μg/kg/min | Drug Load (mg) | 5.64 | 24.18 | 72.54 | 96.72 | 145.08 |
| | Injection (cc) | 0.11 | 0.48 | 1.45 | 1.93 | 2.90 |
| 0.016 μg/kg/min | Drug Load (mg) | 11.27 | 48.30 | 144.90 | 193.20 | 289.80 |
| | Injection (cc) | 0.22 | 0.97 | 2.90 | 3.86 | 5.80 |

TABLE 3

Thermoplastic polymer compositions comprising 15% CGRP

| Delivery Rate | | Duration of release (Days) | | | | |
|---|---|---|---|---|---|---|
| | | 7 | 30 | 90 | 120 | 180 |
| 0.0008 μg/kg/min | Drug Load (mg) | 0.56 | 2.42 | 7.26 | 9.68 | 14.52 |
| | Injection (cc) | 0.004 | 0.02 | 0.05 | 0.065 | 0.097 |
| 0.0032 μg/kg/min | Drug Load (mg) | 2.26 | 9.69 | 29.07 | 38.76 | 58.14 |
| | Injection (cc) | 0.02 | 0.07 | 0.19 | 0.26 | 0.39 |
| 0.008 μg/kg/min | Drug Load (mg) | 5.64 | 24.18 | 72.54 | 96.72 | 145.08 |
| | Injection (cc) | 0.04 | 0.16 | 0.48 | 0.64 | 0.97 |
| 0.016 μg/kg/min | Drug Load (mg) | 11.27 | 48.30 | 144.90 | 193.20 | 289.80 |
| | Injection (cc) | 0.08 | 0.32 | 0.97 | 1.29 | 1.93 |

For example, in one embodiment of the present invention, a polymeric composition comprising 5 wt. % CGRP (i.e., 5.64 mg CGRP) can be formulated to produce a polymer matrix in situ that will deliver CGRP at circulating plasma levels of CGRP up to 157±26 pg/mL or deliver CGRP at a rate of 0.008 μg g/kg/min over a period of 7 days when about 0.11 mL of this composition is administered to a patient (Table 2). Alternatively, if it is desired to have the CGRP delivered at circulating plasma levels of CGRP of 157±26 pg/mL or a rate of 0.008 μg/kg/min over a period of 180 days, a composition comprising 15 wt. % CGRP (i.e., 145.08 mg CGRP) can be prepared and about 0.97 mL of this composition is administered to the patient (Table 3). In a similar fashion, other compositions can be prepared according to the examples shown in Tables 2 and 3 to provide the desired circulating plasma levels of CGRP and delivery rate over the targeted time period. It is to be understood that the formulations in Tables 2 and 3 are provide as examples to illustrate the invention, and it would be well within the skill of persons of ordinary skill in the art to design other formulations that would yield different delivery rates over different time periods.

The compositions of this invention can be delivered directly to a target site and can be designed to provide continuous release of CGRP over a targeted time period so as to reduce the frequency of drug administration. In general, a solid implant or matrix is formed upon dispensing the flowable polymeric composition either into a tissue or onto the surface of a tissue which is surrounded by an aqueous medium. The composition can be delivered to a patient's tissue or bodily fluid by any convenient technique. For example, the thermoplastic polymeric solution can be placed in a syringe and injected through a needle into a patient's body, i.e., in the desired tissue site or bodily fluid. Upon discharge of the composition from the needle into the tissue or fluid, the solvent dissipates or diffuses away from the polymer and into the surrounding fluid, resulting in the precipitation of the biocompatible polymer which precipitate forms a coherent mass or polymer matrix. The polymer matrix can adhere to its surrounding tissue or bone by mechanical forces and can assume the shape of its surrounding cavity and conform to the irregular surface of the tissue. The implant will biograde over time and does not require removal when CGRP is depleted.

In certain instances, formation of the solid matrix from the flowable delivery system is not instantaneous. For example, the process can occur over a period of minutes to several hours. During this period, the rate of diffusion of CGRP from the coagulating polymeric composition may be much more rapid than the rate of release that occurs from the subsequently formed solid matrix. "Initial burst" refers to the release of a CGRP from the polymeric composition during the first 24 hours after the polymeric composition is contacted with an aqueous fluid. This initial "burst" of CGRP that is released during polymer matrix formation may result in the loss or release of a large amount of the active agent. Therefore, in certain embodiments the thermoplastic polymer composition can further comprise a polymeric controlled release additive that substantially reduces the "initial burst" of CGRP released from the polymeric composition during the initial 24 hours after implantation. The use of such an additive is described in U.S. Pat. No. 6,143,314, which is specifically incorporated herein by reference. As used herein, the term "substantially reduces" means a decrease of at least 15%, and preferably between about 15% to about 70%, of CGRP that is released from the polymeric composition compared to a composition without the additive. Examples of suitable controlled release additives include thermoplastic polymers having poly (lactide-co-glycolide) (PLG) moieties and polyethylene glycol (PEG) moieties. In one embodiment, the controlled release additive is a poly(lactide-co-glycolide)/polyethylene glycol (PLG/PEG) block copolymer. The polymeric controlled release additive is present in the polymeric composition in an amount effective to reduce the initial burst of biologically active agent released from the polymeric composition during the first 24 hours after implantation. Preferably, the polymeric composition includes about 1 wt. % to about 50 wt. %, more preferably about 2 wt. % to about 20 wt. % of the polymeric controlled release additive.

The solid matrix is capable of biodegradation, bioerosion and/or bioabsorption within the implant site of the patient or animal, and will slowly biodegrade within the body and will release CGRP contained within its matrix at a controlled rate until depleted. Generally, the polymer matrix will breakdown over a period from about 1 week to about 12 months. The release of CGRP can be affected by the size and shape of the polymer matrix, the loading of drug within the polymer matrix, the permeability factors involving CGRP and the particular polymer, and the degradation of the polymer. The above parameters can be adjusted by one skilled in the art of drug delivery to give the desired rate and duration of release (see for example Tables 2 and 3).

The polymeric CGRP solution can be placed anywhere within the body, including tissue sites such as soft tissue (e.g., muscle or fat), hard tissue (e.g., bone), or a cavity such as the periodontal, oral, vaginal, rectal, or nasal cavity. As used herein, the term "tissue site" includes any tissues in an organism. A tissue site is typically surrounded by an aqueous or body fluid such as subcutaneous tissue, interstitial fluid, blood, serum, cerebrospinal fluid or peritoneal fluid.

A suitable polymeric gel for use in this embodiment comprises ABA- or BAB-type block copolymers, where the A-blocks are relatively hydrophobic A polymer blocks comprising a biodegradable polyester, and the B-blocks are relatively hydrophilic B polymer blocks comprising polyethylene glycol (PEG). The A block is preferably a biodegradable polyester synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic λ-hydroxybutyric acid, δ-valerolactone, δ-hydroxyvaleric acid, hydroxybutyric acids, malic acid, and copolymers thereof, and the B block is PEG. The polymeric gel is preferably biodegradable and exhibits water solubility at low temperatures and undergoes reversible thermal gelation at physiological mammalian body temperatures. Furthermore, these polymeric gels are biocompatible and capable of releasing CGRP entrained within its matrix over time and in a controlled manner. The polymeric gel may be prepared as disclosed in U.S. Pat. No. 6,201,012, which is incorporated herein by reference.

Other suitable polymers include in situ formed hydrogels prepared from thermosensitive block copolymers. Such block copolymers undergo reversion between gel and sol under certain conditions. The gel-sol transition temperature is generally above room temperature, which depends on the composition of the gel, as well as on the chemical structure and molecular weight of PEG or PEG copolymers. The polymer is a poly(ethylene glycol), a derivative thereof, or a copolymer that reacts with the poly(ethylene glycol) segment. The polymer can also be poly(propylene glycol) (PPG) or other poly (alkylene glycols). Higher molecular weight poly(ethylene glycol) is also called poly(ethylene oxide) (PEO). Poly(ethylene glycol) block copolymers with poly(propylene oxide) (PPO), including an pluronic polymers (Poloxamers) may also be used. Different molecular weight of each segment, and weight ratio of the blocks, and different sequences may be used such as PEO-PPO-PEO (Pluronic), PPO-PEO-PPO (Pluronic-R), PEO-PPO, etc.

Suitable polymers useful in the invention include PLURONIC (BASF Corp.) surfactant which is a group of poly (ethylene oxide)-polypropylene oxide)poly(ethylene oxide) triblock copolymers also known as poloxamers. The PEG block at both ends is able to complex with alpha-cyclodextrin, just like the PEG molecules. PLURONIC polymers have unique surfactant abilities and extremely low toxicity and immunogenic responses. These products have low acute oral and dermal toxicity and low potential for causing irritation or sensitization, and the general chronic and subchronic toxicity is low. In fact, PLURONIC polymers are among a small number of surfactants that have been approved by the FDA for direct use in medical applications and as food additives (BASF (1990) Pluronic & Tetronic Surfactants, BASF Co., Mount Olive, N.J.). Recently, several PLURONIC polymers have been found to enhance the therapeutic effect of drugs (March, K. L., et al., *Hum. Gene Therapy* 6(1): 41-53, 1995).

The hydrogel-based injectable composition may be prepared in any suitable manner. Generally, CGRP in aqueous solution is combined with the poly(ethylene glycol) component. The mixture is cooled, generally to a temperature of 0° C. to 25° C. The resulting product is a white viscous hydrogel.

2. Films

This invention further provides a prophylaxis for or method of treating HF and/or renal failure comprising administering biodegradable, biocompatible polymeric film comprising CGRP to a patient. The polymeric films are thin compared to their length and breadth. The films typically have a uniform selected thickness between about 60 micrometers and about 5 mm. Films of between about 600 micrometers and 1 mm and between about 1 mm and about 5 mm thick, as well as films between about 60 micrometers and about 1000 micrometers; and between about 60 and about 300 micrometers are useful in the manufacture of therapeutic implants for insertion into a patient's body. The films can be administered to the patient in a manner similar to methods used in adhesion surgeries. For example, a CGRP film formulation can be sprayed or dropped onto a tissue site during surgery, or a formed film can be placed over the selected tissue site. In an alternative embodiment, the film can be used as sustained release coating on a medical device such as a stent.

Either biodegradable or nonbiodegradable polymers may be used to fabricate implants in which the CGRP is uniformly distributed throughout the polymer matrix A number of suitable biodegradable polymers for use in making the biodegradable films of this invention are known to the art, including polyanhydrides and aliphatic polyesters, preferably polylactic acid (PLA), polyglycolic acid (PGA) and mixtures and copolymers thereof, more preferably 50:50 copolymers of PLA:PGA and most preferably 75:25 copolymers of PLA:PGA. Single enantiomers of PLA may also be used, preferably L-PLA, either alone or in combination with PGA. Polycarbonates, polyfumarates and caprolactones may also be used to make the implants of this invention.

A plasticizer may be incorporated in the biodegradable film to make it softer and more pliable for applications where direct contact with a contoured surface is desired.

The polymeric films of this invention can be formed and used as flat sheets, or can be formed into three-dimensional conformations or "shells" molded to fit the contours of the tissue site into which the film is inserted.

To make the polymeric films of this invention, a suitable polymeric material is selected, depending on the degradation time desired for the film. Selection of such polymeric materials is known to the art. A lower molecular weight, e.g. around 20,000 daltons, 50:50 or 55:45 PLA:PGA copolymer is used when a shorter degradation time is desired. To ensure a selected degradation time, the molecular weights and compositions may be varied as known to the art.

Polymeric films of this invention may be made by dissolving the selected polymeric material in a solvent known to the art, e.g., acetone, chloroform or methylene chloride, using about 20 mL solvent per gram of polymer. The solution is then degassed, preferably under gentle vacuum to remove dissolved air and poured onto a surface, preferably a flat non-stick surface such as BYTAC (Trademark of Norton Performance Plastics, Akron, Ohio) non-stick coated adhesive-backed aluminum foil, glass or TEFLON™. Non-stick polymer. The solution is then dried, preferably air-dried, until it is no longer tacky and the liquid appears to be gone. The known density of the polymer may be used to back-calculate the volume of solution needed to produce a film of the desired thickness.

Films may also be made by heat pressing and melt forming/drawing methods known to the art. For example, thicker films can be pressed to form thinner films, and can be drawn out after heating and pulled over forms of the desired shapes, or pulled against a mold by vacuum pressure.

The amount of CGRP to be incorporated into the polymeric films of this invention is an amount effective to show a measurable effect in treating of preventing HF and/or renal failure. CGRP can be incorporated into the film by various techniques such as by solution methods, suspension methods, or melt pressing.

Solid CGRP implants can also be made into various shapes other than films by injection molding or extrusion techniques. For example, the implant can comprise a core material such as ethylene/vinyl acetate copolymer, and a vinyl acetate content of 20% by weight or more and which functions as a matrix for CGRP, in a quantity which is sufficient for a controlled release of CGRP, and a membrane which encases the core material and also consists of EVA material and an acetate content of less than 20% by weight. The implant can be obtained, for example, by means of a co-axial extrusion process, a method in which the two EVA polymers are extruded co-axially with the aid of a co-axial extrusion head. The co-axial extrusion process is art known per se so that it will not be gone into further within the scope of this description.

3. Encapsulated CGRP

Yet another CGRP controlled release formulation according to this invention comprises very small capsules which can be administered, for example by injection, into body tissue or fluids. Accordingly, this invention further provides a method of treating HF by administering capsules comprising CGRP, and a kit comprising said capsules. The capsules include an encapsulating layer which surrounds CGRP or comprises CGRP dispersed throughout the encapsulating layer. After injection, the encapsulating layer degrades or dissolves, and CGRP is released within the heart. CGRP can also diffuse through the encapsulating layer. The encapsulating layer may be made from various materials including biodegradable polymers in the form of microspheres, or from standard vesicle forming lipids which form liposomes and micelles. Such sustained release CGRP capsules are useful for treatment or prophylaxis of HE and/or renal failure. Both biodegradable and nonbiodegradable polymers may be used to prepare formulations in which CGRP is encapsulated within a polymer matrix and surrounded by a rate-controlling membrane.

a. Microspheres

One embodiment of CGRP-containing capsules comprises solid microparticles formed of the combination of biodegradable polymers with CGRP loadings that yield a sustained release over a period of one day to at least one week, when administered orally, transmucosally, topically or by injection. The microparticles have different diameters depending on their route of administration. For example, microparticles administered by injection have diameters sufficiently small to pass through a needle, in a size range of between 10 and 100 microns. Orally administered microparticles are preferably less than 10 microns in diameter to facilitate uptake by the small intestine. The microspheres can contain from less than 0.01% by weight up to approximately 50% by weight CGRP.

As used herein, "micro" refers to a particle having a diameter of from nanometers to micrometers. Microspheres are solid spherical particles; microparticles are particles of irregular or non-spherical shape. A microsphere may have an outer coating of a different composition than the material originally used to form the microsphere. Thus, the term "microsphere" as used herein encompasses microparticles, microspheres and microcapsules.

Polymers that can be used to form the microspheres include, but are not limited to, biodegradable polymers such as poly(lactic-co-glycolic acid) (PLG), poly(lactic acid) (PLA), poly(caprolactone), polycarbonates, polyamides, polyanhydrides, polyamino acids, polyortho esters, polyacetals, polycyanoacrylates and degradable polyurethanes, and copolymers thereof. Almost any type of polymer can be used provided the appropriate solvent and non-solvent are found which have the desired melting points.

Biodegradable microspheres can be prepared using any of the methods developed for making microspheres for drug delivery, for example, as described by Mathiowitz and Langer (*J. Controlled Release*, 5:13-22 (1987)); Mathiowitz, et al. (*Reactive Polymers*, 6:275-283 (1987)); and Mathiowitz, et al. (*J. Appl. Polymer Sci.*, 35:755-774 (1988)), the teachings of which are incorporated herein. The selection of the method depends on the polymer selection, the size, external morphology, and crystallinity that is desired, as described, for example, by Mathiowitz, et al. (*Scanning Microscopy*, 4:329-340 (1990)); Mathiowitz, et al. (*J. Appl. Polymer Sci.*, 45:125-134 (1992)); and Benita, et al. (*J. Pharm. Sci.* 73:1721-1724 (1984)), the teachings of which are incorporated herein. Methods include solvent evaporation, phase separation, spray drying, and hot melt encapsulation. U.S. Pat. Nos. 3,773,919; 3,737,337; 3,523,906; 4,272,398; 5,019,400; 5,271,961 and 6,403,114 are representative of methods for making microspheres, each of which is specifically incorporated herein by reference. U.S. Pat. No. 5,019,400, which is incorporated herein by reference, describes the Prolease® process in which microspheres can be formed in a size suitable for injection through a 26-gauge needle, (less than 50 micrometers in diameter). The process described in U.S. Pat. No. 5,019,400 has the advantage of achieving drug encapsulation in the absence of water at very low temperatures. These conditions are particularly suitable for fragile macromolecules such as proteins, where maintaining stability is a concern. Microparticles can be formed by either a continuous freezing and extraction process or by a batch process wherein a batch of frozen microdroplets is formed in a first step, and then in a separate second step, the frozen microdroplets in the batch are extracted to form microparticles. U.S. Pat. No. 6,403,114 describes a method of preparing microspheres in commercial batch sizes, and U.S. Pat. No. 5,271,961 describes a continuous method of preparing microspheres. Each of these patents are incorporated herein by reference In general, microspheres can be prepared by combining CGRP, the polymer and a solvent to form a droplet, and then removing the solvent to yield microspheres that are hardened, dried, and collected as a free-flowing powder. Prior to administration to the patient, the powder is suspended in a diluent and then injected into the patient. Release of CGRP from the microsphere is governed by diffusion of CGRP through the polymer matrix and by biodegradation of the polymer. The release kinetics can be modulated through a number of formulation and fabrication variables including polymer characteristics and the addition of excipients and release modifiers. In solvent evaporation, described in U.S. Pat. No. 4,272,398, which is incorporated herein by reference, the polymer is dissolved in a volatile organic solvent. The CGRP, either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres. After loading the solution with CGRP, the solution is suspended in distilled water containing 1% (w/y) poly(vinyl alcohol), after which the solvent is evaporated and resulting microspheres are dried overnight in a lyophilizer. Microspheres with different sizes (1-1000 microns) and morphologies can be obtained by this method which is useful for relatively stable polymers such as polyesters and polystyrene.

Polymer hydrolysis is accelerated at acidic or basic pH's and thus the inclusion of acidic or basic excipients can be used to modulate the polymer erosion or degradation rate. The excipients can be added as particulates, can be mixed with the incorporated CGRP or can be dissolved within the polymer.

Degradation modulators can also be added to the microparticle formulation, and the amount added is based on weight relative to the polymer weight. They can be added to the formulation as a separate phase (i.e., as particulates) or can be codissolved in the polymer phase depending on the compound. In all cases the amount of enhancer added is preferably between 0.1 and thirty percent (w/w, polymer). Types of degradation modulators include inorganic acids such as ammonium sulfate and ammonium chloride, organic acids such as citric acid, benzoic acids, heparin, and ascorbic acid, inorganic bases such as sodium carbonate, potassium carbonate, calcium carbonate, zinc carbonate, and zinc hydroxide, and organic bases such as protamine sulfate, sperinine, choline, ethanolamine, diethanolamine, and triethanolamine and surfactants such as Tween™ and Pluronic™.

Stabilizers can be also added to the formulations to maintain the potency of CGRP depending on the duration of release. Stabilizers include carbohydrates, amino acids, fatty acids, and surfactants and are known to those skilled in the art. In addition, excipients which modify the solubility of CGRP such as salts complexing agents (albumin, protamine) can be used to control the release rate of the protein from the microparticles.

In one embodiment for the treatment or prophylaxis of HF and/or renal failure, the patient is administered CGRP incorporated in microparticles which degrade over a period of 1 of 2 months. The microparticles preferably range in size from 10 to 60 microns, and can be injected using a puncture needle with the aid of a suspension media. One example of a suspension media comprises 3% methyl cellulose, 4% mannitol, and 0.1% Tween™80.

In a further embodiment, microparticles containing CGRP can be embedded in a gel matrix as described in U.S. Pat. No. 6,589,549, which is incorporated herein by reference. In this embodiment, CGRP (alone or in combination with one or more additional agents) may be located in the microparticle alone or both in the microparticle and the gel matrix. The microparticle-gel delivery system can release CGRP over a prolonged period of time at a relatively constant rate. The release profile of the system can be modified by altering the microparticle and/or the gel composition. After injection, the gel sets and localizes the microparticle suspended in it. CGRP encapsulated in the microparticle must be released from the microparticle before traveling through the gel matrix and entering the biological system. Therefore, the immediate release, or the burst, associated with microparticle delivery systems can be reduced and modulated. Since the release rates of CGRP from these two systems can be quite different, embedding microparticles in the gel phase offers additional modulation and economical use of CGRP. The benefits include higher bioavailability and longer duration of action than either system when used alone. Moreover, the combined system can improve the safety of microparticle dosage form. A suitable polymeric gel for use in this embodiment comprises ABA- or BAB-type block copolymers, where the A-blocks are relatively hydrophobic A polymer blocks comprising a biodegradable polyester, and the B-blocks are relatively hydrophilic B polymer blocks comprising polyethylene glycol (PEG). The A block is preferably a biodegradable polyester synthesized from monomers selected from the group consisting of D,L-lactide, D-lactide, L-lactide, D,L-lactic acid, D-lactic acid, L-lactic acid, glycolide, glycolic acids ε-caprolactone, ε-hydroxyhexanoic λ-hydroxybutyric acid, δ-valerolactone, δ-hydroxyvaleric acid, hydroxybutyric acids, malic acid, and copolymers thereof, and the B block is PEG. The polymeric gel is preferably biodegradable and exhibits water solubility at low temperatures and undergoes reversible thermal gelation at physiological mammalian body temperatures. Furthermore, these polymeric gels are biocompatible and capable of releasing CGRP entrained within its matrix over time and in a controlled manner. The polymeric gel may be prepared as disclosed in U.S. Pat. No. 6,201,072, which is incorporated herein by reference.

b. Solid Implants

Solid implants made by injection molding or extrusion method similar to that used to manufacture Norplant™, a product brand and a trademark of Leiras Co., which is based on a non-degradable polymeric material. In this embodiment, a definitely formed, device constructed of silicone rubber which is implanted into the body by a surgical operation, and it is removed therefrom in a similar manner after a defined time when the active component has been released and diffused to the body. Any of the polymeric materials utilized for the construction of implantable devices may be used in the practice of the invention. A broad class of silicone elastomers can be used to form the silicone-elastomer drug matrix. Suitable silicone elastomers in accordance with the present invention include SILASTIC™ and R-2602 RTV silicone elastomer available from Nusil Silicone Technology (Carpinteria, Calif.). The silicone elastomers can be catalyzed so that polymerization and formation of the core is accomplished at room temperature. The core may also be formed by heat curable core material. Generally, the silicone implantable depots are constructed of polydimethylsilicone (PDMS). See, for example, U.S. Pat. Nos. 4,957,119 and 5,088,505, which are incorporated herein by reference. A typical material is dimethylpolysiloxane (Silgel™ 601, Wacker Chemie GmbH), an addition cross-linking two-component composition of nine pats of component A and one part of component B. Dimethyldiphenylpolysiloxane, dimethylpolysiloxanol or silicone copolymers may also be employed. Other suitable polymeric materials are the porous, ethylene/vinyl acetate copolymers which have been utilized to construct depots for the implantable release of hydrophilic biologically active substances such as proteins through the pores thereof. Biodegradable polymers may also be used to form the solid implants using extrusion or injection molding processes.

c. Liposomes

Another method of delivering CGRP to a patient is accomplished with encapsulation by liposomes, wherein CGRP may be sequestered in the liposome membrane or may be encapsulated in the aqueous interior of the vesicle. The term "liposome" refers to an approximately spherically shaped bilayer structure, or vesicle, comprised of a natural or synthetic phospholipid membrane or membranes that contain two hydrophobic tails consisting of fatty acid chains, and sometimes other membrane components such as cholesterol and protein, which can act as a physical reservoir for CGRP. Upon exposure to water, the phospholipid molecules spontaneously align to form sphercal, bilayer membranes with the lipophilic ends of the molecules in each layer associated in the center of the membrane and the opposing polar ends forming the respective inner and outer surface of the bilayer membrane(s). Thus, each side of the membrane presents a hydrophilic surface while the interior of the membrane comprises a lipophilic medium. These membranes may be arranged in a series of concentric, spherical membranes separated by thin strata of water around an internal aqueous space. These multilamellar vesicles (MLV) can be converted into small or unilamellar vesicles (UV), with the application of a shearing force. Liposomes are characterized according to size and number of membrane bilayers. Vesicle diameters can be large (>200 nm) or small (<50 nm) and the bilayer can have unilamellar, oligolamellar, or multilamellar membrane.

The selection of lipids is generally guided by considerations of liposome size and ease of liposome sizing, and lipid and CGRP release rates from the site of liposome delivery. Typically, the major phospholipid components in the liposomes are phosphatidylcholine (PC), phosphatidylglycerol (PG), phosphatidyl serine (PS), phosphatidylinositol (PI) or egg yolk lecithin (EYL). PC, PG, PS, and PI having a variety of acyl chains groups or varying chain lengths are commercially available, or may be isolated or synthesized by known techniques.

Current methods of drug delivery by liposomes require that the liposome carrier will ultimately become permeable and release the encapsulated drug. This can be accomplished in a passive manner in which the liposome membrane degrades over time through the action of agents in the body. Every liposome composition will have a characteristic half-life in the circulation or at other sites in the body. In contrast to passive drug release, active drug release involves using an agent to induce a permeability change in the liposome vesicle. In addition, liposome membranes can be made which become destabilized when the environment becomes destabilized near the liposome membrane (*Proc. Nat. Acad. Sci.,* 84:7851 (1987); *Biochemistry,* 28:9508, (1989)). For example, when liposomes are endocytosed by a target cell they can be routed to acidic endosomes which will destabilize the liposomes and result in drug release. Alternatively, the liposome membrane can be chemically modified such that an enzyme is placed as a coating on the membrane which slowly destabilizes the liposome (*The FASEB Journal,* 4:2544 (1990)). It is also well known that lipid components of liposomes promote peroxidative and free radical reactions which cause progressive degradation of the liposomes, and has been described in U.S. Pat. No. 4,797,285. The extent of free radical damage can be reduced by the addition of a protective agent such as a lipophilic free radical quencher is added to the lipid components in preparing the liposomes. Such protectors of liposome are also described in U.S. Pat. No. 5,190,761, which also describes methods and references for standard liposome preparation and sizing by a number of techniques. Protectors of liposomal integrity will increase the time course of delivery and provide for increased transit time within the target tissue.

Liposomes for use in the present invention can be prepared by any of the various techniques presently known in the art. Typically, they are prepared from a phospholipid, for example, distearoyl phosphatidylcholine, and may include other materials such as neutral lipids, for example, cholesterol, and also surface modifiers such as positively charged (e.g., sterylamine or aminomannose or aminomannitol derivatives of cholesterol) or negatively charged (e.g., diacetyl phosphate, phosphatidyl glycerol) compounds. Multilamellar liposomes can be formed by conventional techniques, that is, by depositing a selected lipid on the inside wall of a suitable container or vessel by dissolving the lipid in an appropriate solvent, and then evaporating the solvent to leave a thin film on the inside of the vessel or by spray drying. An aqueous phase is then added to the vessel with a swirling or vortexing motion which results in the formation of MLVs. UVs can then be formed by homogenization, sonication or extrusion (through filters) of MLV's. In addition, UVs can be formed by detergent removal techniques The liposomes containing CGRP can be delivered within biodegradable microdrug delivery systems such as larger more stable liposomes or other fully encapsulated controlled release system, such as a biodegradable impermeable polymer coatings. The time course of release is governed then by the additive time delay of the barriers that separate CGRP from the host, as well as their combined transport pathways. Microsphere delivery systems could also be used.

4. CGRP Conjugates

A further aspect of this invention includes CGRP conjugated to polymers, and to methods of treating HF and/or renal failure by administering a CGRP conjugate to a patient. It is known that many potentially therapeutic proteins have been found to have a short half life in the blood serum. For the most part, proteins are cleared from the serum through the kidneys. Small molecules that normally would be excreted through the kidneys are maintained in the blood stream if their size is increased by attaching a biocompatible polymer such as a PEG derivative. Proteins and other substances that create an immune response when injected can be hidden to some degree from the immune system by coupling of a polymer to the protein. Accordingly, another embodiment of this invention comprises a method of treating HF by administering a conjugate comprising CGRP coupled to a biocompatible, non-immunogenic polymer. As used herein, the term "conjugate" refers to a CGRP molecule covalently or noncovalently coupled to one or more polymers. These conjugates are substantially non-immunogenic and retain at least 75%, preferably 85%, and more preferably 95% or more of the activity of unmodified CGRP.

Examples of polymers that can be coupled to CGRP include, but not limited to, biological polymers (e.g., polysaccharides, polyamides, pharmacologically inert nucleotide components, etc.), and derivatives of biological polymers, or non-biological polymers. Specific examples include poly (alkylene glycols) such as poly(ethylene glycol) MPEG), poly-lactic acid (PLA), poly-glycolic acid, poly($\epsilon$-caprolactone), poly($\beta$-hydroxybutyrate), poly($\beta$-hydroxyvalerate), polydioxanone, poly(malic acid), poly(tartronic acid), poly (ortho esters), polyanhydrides, polycyanoacrylates, poly (phosphoesters), polyphosphazenes, hyaluronidate, polysulfones, polyacrylamides, polymethacrylate, chimeric recombinant elastin-silk protein (Protein Polymers, Inc.) and collagen (Matrix Pharmaceuticals, Inc.). In a preferred embodiment CGRP is conjugated to PEG or a polysaccharide.

As used herein the term "PEG" includes to straight or branched polyethylene glycol oligomer and monomers (PEG subunits) and also includes polyethylene glycol oligomers that have been modified to include groups which do not eliminate the amphiphilic properties of such oligomer, e.g. without limitation, alkyl, lower alkyl, aryl, amino-alkyl and amino-aryl. The term "PEG subunit" refers to a single polyethylene glycol unit, i.e., $—(CH_2CH_2O)—$.

Reactive sites that form the loci for attachment of polymers to CGRP are dictated by the protein's structure. Many polymers react with free primary amino groups or thiol groups of the polypeptide. Covalent attachment of the polymers to CGRP may be accomplished by known chemical synthesis techniques. In one embodiment of the invention, CGRP may be conjugated via a biologically stable, nontoxic, covalent linkage to one or more strands of PEG. Such linkages may include urethane (carbamate) linkages, secondary amine linkages, and amide linkages. Various activated PEGs suitable for such conjugation are available commercially from Shearwater Polymers, Huntsville, Ala.

5. Transdermal Delivery

CGRP may also be administered to a patient via transdermal delivery devices, patches, electrophoretic devices, bandages and the like. Such transdermal patches may be used to provide continuous or discontinuous infusion of CGRP in controlled amounts. The construction and use of transdermal patches for the delivery of pharmaceutical agents is well known in the art. See, for example, U.S. Pat. No. 5,023,252, the disclosure of which is herein incorporated by reference. Such patches may be constructed for continuous, pulsatile, or on-demand delivery of CGRP. For example, a dose of CGRP or a pharmaceutically acceptable composition thereof may be combined with skin penetration enhancers including, but not limited to, oleic acid, oleyl alcohol, long chain fatty acids, propylene glycol, polyethylene glycol, isopropanol, ethoxydiglycol, sodium xylene sulfonate, ethanol, N-methylpyrrolidone, laurocapram, alkanecarboxylic acids, dimethylsulfoxide, polar lipids, N-methyl-2-pyrrolidone, and the like, which increase the permeability of the skin to the dose of CGRP and permit the dose of CGRP to penetrate through the skin and into the bloodstream. CGRP or a pharmaceutically acceptable composition thereof may be combined one or more agents including, but not limited to, alcohols, moisturizers, humectants, oils, emulsifiers, thickeners, thinners, surface active agents, fragrances, preservatives, antioxidants, vitamins, or minerals. CGRP or a pharmaceutically acceptable composition thereof may also be combined with a polymeric substance including, but not limited to, ethylcellulose, hydroxypropyl cellulose, ethylene/vinylacetate, polyvinyl pyrrolidone, and the like, to provide the composition in gel form, which may be dissolved in solvent such as methylene chloride, evaporated to the desired viscosity, and then applied to backing material to provide a patch. The backing can be any of the conventional materials such as polyethylene, ethyl-vinyl acetate copolymer, polyurethane and the like.

6. Transmucosal Delivery

CGRP may also be administered transmucosally, i.e., to and across a mucosal surface, for example, for the treatment of angina. Transmucosal administration of a source of CGRP or a pharmaceutically acceptable composition thereof can be accomplished generally by contacting an intact mucous membrane with a source of CGRP or a pharmaceutically acceptable composition thereof, and maintaining the source in contact with the mucous membrane for a sufficient time period to induce the desired therapeutic effect. Preferably CGRP or a pharmaceutically acceptable composition thereof is administered to the oral or nasal mucosa such as the buccal mucosa, the sublingual mucosa, the sinuidal mucosa, the gum, or the inner lip. Particularly, the source of CGRP is any preparation usable in oral, nasal, sinuidal, rectal or vaginal cavities that can be formulated using conventional techniques well known in the art. For example, the preparation can be a buccal tablet, a sublingual tablet, a spray, and the like that dissolves or disintegrates, delivering drug into the mouth of the patient. A spray or drops can also be used to deliver the CGRP or a pharmaceutically acceptable composition thereof to nasal or sinuidal cavities. The preparation may or may not deliver the drug in a sustained fashion. Examples for manufacturing such preparations are disclosed, for example, in U.S. Pat. No. 4,764,378, which is specifically incorporated herein by reference. The preparation can also be a syrup that adheres to the mucous membrane. Suitable mucoadhesives include those well known in the art such as polyacrylic acids, preferably having the molecular weight between from about 450,000 to about 4,000,000, e.g., Carbopol™ 934P; sodium carboxymethylcellulose (NaCMC), hydroxypropylmethylcellulose (HPMC), e.g. Methocel™ K100, and hydroxypropylcellulose.

The transmucosal preparation can also be in the form of a bandage, patch, and the like that contains the drug and adheres to a mucosal surface. A mucoadhesive preparation is one that upon contact with intact mucous membrane adheres to the mucous membrane for a sufficient time period to induce the desired therapeutic effect. Suitable transmucosal patches are described for example in PCT Publication WO 93/23011, which is specifically incorporated herein by reference. A suitable patch may comprise a backing which can be any flexible film that prevents bulk fluid flow and provides a barrier for to loss of the drug from the patch. The backing can be any conventional material such as polyethylene, ethyl-vinyl acetate copolymer, polyurethane and the like. In a patch involving a matrix which is not itself a mucoadhesive, the drug-containing matrix can be coupled with a mucoadhesive component (such as a mucoadhesive described above) in order that the patch may be retained on the mucosal surface. Suitable configurations include a patch or device wherein the matrix has a smaller periphery than the backing layer such that a portion of the backing layer extends outward from the periphery of the matrix. A mucoadhesive layer covers the outward extending portion of the backing layer such that the underside of the backing layer carries a layer of mucoadhesive around its periphery. The backing and the peripheral ring of mucoadhesive taken together form a reservoir which contains a drug-containing matrix (e.g. a tablet, gel or powder). It may be desirable to incorporate a barrier element between the matrix and the mucoadhesive in order to isolate the mucoadhesive from the matrix. The barrier element is preferably substantially impermeable to water and to the mucosal fluids that will be present at intended site of adhesion. A patch or device having such barrier element can be hydrated only through a surface that is in contact with the mucosa, and it is not hydrated via the reservoir. Such patches can be prepared by general methods well known to those skilled in the art. The preparation can also be a gel or film comprising a mucoadhesive matrix as described for example in PCT Publication WO 96/30013, which is specifically incorporated herein by reference.

7. Implantable Pumps

In another embodiment, CGRP can be suitably administered using an implantable pump, which is particularly applicable for outpatient treatment. For example, a constant rate pump may be used to provide a constant, unchanging delivery of CGRP over a period of time. Alternatively, a programmable, variable rate pump may be used if changes to the infusion rate are desired. Constant rate and programmable pumps are well know in the art and need not be described further.

CGRP may also be released or delivered from an implantable osmotic mini-pump such as that described in U.S. Pat. Nos. 5,728,396, 5,985,305, 6,358,247, and 6,544,252, the disclosures of which are specifically incorporated herein in their entirety. The release rate from an osmotic mini-pump may be modulated with a microporous, fast-response gel disposed in the release orifice for controlled release or targeted deliver of CGRP. Osmotic pumps are preferred in that they are much smaller than the constant rate and programmable pumps.

In one embodiment, the osmotic pump comprises a miniature drug-dispensing system that operates like a miniature syringe and releases minute quantities of concentrated CGRP formulations in a continuous, consistent flow over months or years. The system is implanted under the skin and can be as small as 4 mm OD×44 mm in length or smaller. Such a system is sold under the trademark DUROS® by ALZA Corporation. In brief, such an osmotic delivery system comprises a capsule having an interior that contains the CGRP and ah osmotic agent, a semi-permeable body that permits liquid to permeate through the body to the osmotic agent, and a piston located within the interior of the capsule that defines a movable seal within the interior that separated the osmotic agent from the CGRP.

Augmentation of Current HF Therapies

A further aspect of this invention provides a method of treating HF by administering CGRP according to any of the methods disclosed herein to augment current HF therapies. CGRP can be administered according to any of the dosing regimes of this invention together with one or more addition drugs for HF, wherein CGRP and the additional drug(s) can be administered together, separately and simultaneously, or separately in any order.

Acute Myocardial Infarction

In the treatment of acute MI, physicians take aggressive action to restore blood flow to the heart to minimize permanent ischemic damage. These treatments take the form of vasodilators (nitroglycerin) and antithrombolytics. (streptokinase, tPA), and platelet aggregation inhibitors (gpIIb/IIIa) in the attempt to dilate the coronary arteries and dissolve the thrombus, and inhibit platelet aggregation. If treatment is successful in restoring blood flow, the patient may be sent to recover in the CCU or go to the catheterization lab for an angioplasty or stenting procedure to open any remaining occlusions. However, the ischemic event itself causes generation of free radicals, and this process is potentiated when the vessels are re-opened and blood flow restored, which results in further tissue damage. In this setting, CGRP therapy administered alone or in conjunction with other therapeutic interventions according to any of the methods of this invention, particularly the infusion methods, would augment the current therapies such as antithrombolytics by elevating the therapeutic benefits of these drugs. The cardioprotective benefits of CGRP when infused at the initial stages of evaluation and treatment would provide levels of CGRP suitable to minimize reperfusion injury when interventional therapy is initiated, and thus maximize positive acute and long-term recovery outcomes.

Accordingly, this invention further provides a method of counteracting ischemia due to myocardial infarction in a patient, comprising delivering to said patient an amount of CGRP effective to provide cardioprotection, reduction in infarction size, reduction in reperfusion injury, symptomatic relief, and/or prevent exacerbation of symptoms, wherein said CGRP is delivered to said patient as a controlled release composition.

Percutaneous Translumenal Coronary Angioplasty (PTCA) and Stenting

If antithrombolytic therapy is ineffectual in the emergency room, or if it is determined that elective PTCA intervention is required to restore blood flow, CGRP infusion therapy already in process in the emergency room or started in the catheterization lab would provide the same reperfusion benefits as those described above when blood flow is restored to the ischemic tissues. Additional benefits in the catheterization lab would be realized when CGRP infusion therapy locally dilates coronary blood vessels, decreases the incidence of vasospasms and no-reflow during procedures, increases renal blood flow, and assists in preventing platelet aggregation and smooth muscle cell proliferation at the acute time points (<24 hours) following PTCA. Currently, Reopro® or Integrillin® is administered in advance or during PTCA procedures to halt platelet aggregation and reduce the incidence of restenosis in the long-term (>48 hours). CGRP infusion therapy would augment these current restenosis therapies by elevating the therapeutic benefits of preventing reperfusion injury, as well as inhibiting platelet aggregation and smooth muscle cell proliferation in the acute-term (<24, hours).

Coronary Artery Bypass Surgery (CABG)

Whether CABG is performed as an emergency procedure or as elective surgery, CGRP infusion therapy would provide all of the benefits stated above with respect to acute MI treatment and PTCA procedures. As a result, a CABG procedure could potentially experience even great positive outcomes and fewer acute-term complications.

Coronary Care Unit (CCU) Recovery

CGRP infusion therapy in CCU patients would maximize the ability of CGRP to reduce infarction size and promote cardiac tissue salvage. Whether the therapy was initiated in the emergency room, the cauterization lab, the operating room, or the CCU, recovery and healing process will begin in the CCU where CGRP can be administered over the course of several days, and the long-term benefits of CGRP infusion therapy will realized.

Kits

The present invention also provides pharmaceutical kits for treating HF and/or improving renal function, comprising one or more containers comprising one or more CGRP compositions of this invention. Such kits can also include additional drugs or therapeutics (e.g., antiproliferative or anti-clotting agents, or other compounds used to treat cardiovascular diseases and the like) for co-use with CGRP for treatment or prevention of HF and/or for improving renal failure. In this embodiment, the CGRP and the drug can be formulated in admixture in one container, or can be contained in separate containers for simultaneous or separate administration. The kit can further comprise a device(s) for administering the compounds and/or compositions, and written instructions in a form prescribed by a governmental agency regulating the manufacture, use or sale of pharmaceuticals or biological products, which instructions can also reflect approval by the agency of manufacture, use or sale for human administration.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of treating heart failure in a patient, comprising delivering to said patient CGRP in an amount effective to provide symptomatic relief, or delay progression of the disease state of heart failure in said patient, wherein said CGRP is delivered to said patient as a controlled release composition, wherein said controlled release composition comprises a flowable thermoplastic polymer composition comprising a biocompatible polymer, a biocompatible solvent and CGRP and said composition is delivered to a bodily tissue or fluid in said patient, wherein the amounts of the polymer and the solvent are effective to form a biodegradable polymer matrix containing CGRP in situ when said composition contacts said bodily fluid tissue or fluid, wherein the polymer matrix comprises between about 5% and 15% CGRP by weight and said CGRP is released from said polymer matrix at a rate that will maintain circulating plasma levels of CGRP between 11±5 pg/ml and 186±127 pg/ml over a period of 7 to 180 days.

2. The method of claim 1, wherein said CGRP is in the form of a conjugate comprising CGRP coupled to a polymer.

3. The method of claim 2, wherein said polymer is a poly(alkylene glycol) or a polysaccharide.

4. The method of claim 1, wherein the composition further comprises a controlled release additive.

5. The method of claim 1, wherein said composition comprises between about 0.56 and 290 mg CGRP and between about 0.01 and 5.8 mL of said composition is administered to said patient.

6. The method of claim 1, wherein said composition comprises about 0.56 and 290 mg CGRP and between about 0.004 and 1.93 mL of said composition is administered to said patient.

7. The method of claim 1, wherein said biocompatible polymer is selected from the group consisting of polylactides, polyglycolides, polyanhydrides, polyorthoesters, polycaprolactones, polyamides, polyurethanes, polyesteramides, polydioxanones, polyacetals, polyketals, polycarbonates, polyorthocarbonates, polyphosphazenes, polyhydroxybutyrates, polyhydroxyvalerates, polyalkylene oxalates, polyacrylates, polyalkylene succinates, poly(malic acid), poly(amino acids) and copolymers, terpolymers, cellulose diacetate, ethylene vinyl alcohol, and copolymers and combinations thereof.

8. The method of claim 1, wherein the polymer matrix releases CGRP by diffusion, erosion, or a combination of diffusion or erosion as the polymer matrix biodegrades in said patient.

9. The method of claim 1, wherein said CGRP is delivered via a puncture needle or catheter.

10. The method of claim 1, further comprising administering one or more drugs selected from the group consisting of anti-proliferative agents, anti-clotting agents, vasodilators, diuretics, beta-blockers, calcium ion channel blockers, blood thinners, cardiotonics, ACE inhibitors, anti-inflammatories, and antioxidants.

11. The method of claim 10, wherein said drug is added to said polymer composition prior to administration such that said solid polymer matrix further contains said drug.

12. The method of claim 10, wherein said drug is administered as a separate formulation before, simultaneously, or subsequently to administration of said polymer composition.

13. The method of claim 1, wherein the length of said treatment is sufficient to relieve or attenuate one or more symptoms of heart failure.

14. The method of claim 1, wherein said treatment is sufficient to improve the quality of life of said patient.

15. The method of claim 1, wherein said patient is a pediatric patient.

16. The method of claim 1, wherein said controlled release composition comprises biodegradable microspheres incorporating CGRP.

17. The method of claim 16, wherein said microspheres comprise poly(lactic-co-glycolic acid), poly(lactic acid), poly(caprolactone), polycarbonates, polyamides, polyanhydrides, polyamino acids, polyortho esters, polyacetals, polycyanoacrylates degradable polyurethanes, polyacrylates, ethylene-vinyl acetate copolymers, acyl substituted cellulose acetates, and derivatives and copolymers thereof.

18. The method of claim 16, wherein said CGRP is in the form of a conjugate comprising CGRP coupled to a polymer.

19. The method of claim 16, wherein said microspheres are embedded in a gel matrix.

20. The method of claim 19, wherein said CGRP is in the form of a conjugate comprising CGRP coupled to a polymer.

21. The method of claim 19, wherein said polymer is a poly(alkylene glycol) or a polysaccharide.

22. The method of claim 1, wherein said controlled release composition comprises CGRP conjugated to a polymer.

23. A method of treating heart failure in a patient, comprising administering a flowable composition comprising a biocompatible polymer, a biocompatible solvent and CGRP to a bodily tissue or fluid in said patient, wherein the amounts of the polymer and the solvent are effective to form said polymer matrix comprising CGRP in situ when the formulation contacts said bodily fluid tissue or fluid wherein polymer matrix comprises between about 5% and 15% CGRP by weight and said CGRP is released from said polymer matrix at a rate between about 0.0008 and 0.016 µg/min/kg body weight over a period of 7 to 180 days.

24. The method of claim 1, comprising:
(a) administering CGRP to said patient by a method selected from parenteral, oral, sublingual, intranasal, intracoronary, intra-arterial, intravenous, transmucosal, or intradermal delivery for a time and at a dose effective to provide symptomatic relief, or delay progression of the disease state of heart failure in said patient.

25. The method of claim 24, wherein said controlled release formulation comprises biodegradable microspheres incorporating CGRP.

26. The method of claim 24, wherein said controlled release formulation comprises CGRP coupled to a polymer.

* * * * *